US011065003B2

(12) United States Patent
Aramaki et al.

(10) Patent No.: US 11,065,003 B2
(45) Date of Patent: Jul. 20, 2021

(54) TREATMENT METHOD FOR JOINING BIOLOGICAL ORGANS

(71) Applicant: TERUMO KABUSHIKI KAISHA, Tokyo (JP)

(72) Inventors: Naoki Aramaki, Kanagawa (JP); Miho Kai, Kanagawa (JP); Mayu Hata, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 185 days.

(21) Appl. No.: 16/355,465

(22) Filed: Mar. 15, 2019

(65) Prior Publication Data
US 2019/0282235 A1 Sep. 19, 2019

(30) Foreign Application Priority Data

Mar. 19, 2018 (JP) .............................. JP2018-051459
Sep. 27, 2018 (JP) .............................. JP2018-182132

(51) Int. Cl.
*A61B 17/11* (2006.01)
*A61B 17/115* (2006.01)
*A61B 17/00* (2006.01)

(52) U.S. Cl.
CPC ....... *A61B 17/1114* (2013.01); *A61B 17/1155* (2013.01); *A61B 17/00234* (2013.01); *A61B 2017/00818* (2013.01); *A61B 2017/1132* (2013.01)

(58) Field of Classification Search
CPC ............... A61B 17/1114; A61B 1/1155; A61B 17/07292; A61B 17/068

USPC ....................................................... 227/180.1
See application file for complete search history.

(56) References Cited

U.S. PATENT DOCUMENTS

| | | | |
|---|---|---|---|
| 8,225,799 B2 * | 7/2012 | Bettuchi ............ | A61B 17/1152 128/898 |
| 8,388,692 B2 | 3/2013 | Nakamura et al. | |
| 2004/0260315 A1 * | 12/2004 | Dell ....................... | A61F 2/0063 606/151 |
| 2009/0120994 A1 * | 5/2009 | Murray ................. | A61B 17/115 227/180.1 |
| 2010/0016888 A1 * | 1/2010 | Calabrese ............. | C08G 63/916 606/219 |
| 2011/0282446 A1 * | 11/2011 | Schulte ............... | A61B 17/1155 623/11.11 |

(Continued)

FOREIGN PATENT DOCUMENTS

| | | |
|---|---|---|
| JP | 2004-509205 | 3/2004 |
| JP | 2007-505708 | 3/2007 |

(Continued)

*Primary Examiner* — Nathaniel C Chukwurah
(74) *Attorney, Agent, or Firm* — Thaine Lennox-Gentle; Sheridan Ross, PC

(57) ABSTRACT

Provided is a treatment method that reduces risk factors contributing to anastomotic leakage by using a medical device. The treatment method includes placing a medical device including a sheet-like main body portion for promoting adhesion between biological tissues between one joint target site and another joint target site of a biological organ to be joined, and joining the one joint target site and the other joint target site to each other in a state where at least a portion of the main body portion is interposed between the one joint target site and the other joint target site.

19 Claims, 26 Drawing Sheets

(56) References Cited

U.S. PATENT DOCUMENTS

2014/0358167 A1* 12/2014 Armstrong ....... A61B 17/07292
606/153
2015/0238192 A1* 8/2015 Bettuchi ............ A61B 17/1152
606/153

FOREIGN PATENT DOCUMENTS

| JP | 2008-514719 | 5/2008 |
| JP | 2011-528275 | 11/2011 |
| WO | WO 02/22737 | 3/2002 |
| WO | WO 2005/027983 | 3/2005 |
| WO | WO 2006/039336 | 4/2006 |
| WO | WO 2008/001952 | 12/2009 |
| WO | WO 2010/009335 | 1/2010 |

* cited by examiner

TREATMENT METHOD FOR JOINING BIOLOGICAL ORGANS

CROSS REFERENCE TO RELATED APPLICATIONS

The present application claims the benefit of priority, under 35 U.S.C. § 119, to Japanese Patent Application No. 2018-051459, filed Mar. 19, 2018, and Japanese Patent Application No. 2018-182132, filed Sep. 27, 2018. The entire disclosures of the applications listed above are hereby incorporated herein by reference, in their entirety, for all that they teach and for all purposes.

TECHNICAL FIELD

The present disclosure relates to a treatment method for joining biological organs to each other.

BACKGROUND

In the medical field, the general medical procedure (for example, anastomosis of a digestive tract) of joining biological organs to each other by performing a surgical operation is known. In a case where the medical procedure as described above is performed, as a prognosis determinant after surgery, it is important that there is no delay in adhesion at the joint site between the biological organs joined.

In the medical procedure of joining the biological organs, various methods and various medical devices may be used. For example, a method of suturing the biological organs by using a biodegradable suture, or a method of using a mechanical anastomosis device (refer to Japanese Patent Application JP-T-2007-505708, the entire contents of which are hereby incorporated herein by reference for all that it teaches and for all purposes) for suturing the biological organs by using a stapler has been proposed. In particular, in a case where anastomosis is performed using the mechanical anastomosis device, compared to a method of using the suture, a joining force between the biological organs can be improved at the joint site. Accordingly, the risk factors contributing to an anastomotic leakage can be reduced.

SUMMARY

Technical Problem

However, the degree of progress of adhesion in a joint site depends on the state of biological tissues in sites to be joined (joint target sites) in a patient. Therefore, for example, even in a case where the anastomosis device as disclosed in Japanese Patent Application JP-T-2007-505708 is used, depending on the state of the biological tissues of the patient, there is a possibility that risk factors contributing to anastomotic leakage cannot be sufficiently reduced.

Therefore, the present disclosure describes a treatment method which can reduce the risk factors contributing to anastomotic leakage through a method using a predetermined medical device.

Solution to the Problem

According to an aspect of the present disclosure, a treatment method is described that comprises placing a medical device including a sheet-like main body portion for promoting adhesion between biological tissues between a first joint target site and a second joint target site of a biological organ to be joined, and joining the first joint target site and the second joint target site to each other in a state where at least a portion of the main body portion of the medical device is interposed between the first joint target site and the second joint target site.

Non-Exhaustive Advantages:

According to the present disclosure, the risk factors of an anastomotic leakage after a medical joining procedure can be reduced through a method of interposing a sheet-like main body portion included in a medical device between a first joint target site and a second joint target site. In some embodiments, this joint may comprise a continuous seal between the first joint target site and the second joint target site around at least a portion of the periphery of the main body portion.

DETAILED DESCRIPTION

Hereinafter, embodiments according to the present disclosure will be described with reference to the accompanying drawings.

A treatment method according to the present disclosure relates to a method of joining predetermined sites of a biological organ as a joint object (for example, anastomosis of a digestive tract). First, referring to FIGS. 1 to 8, embodiments of a medical device which can be used for the treatment method according to the present disclosure will be described.

Figure 1:
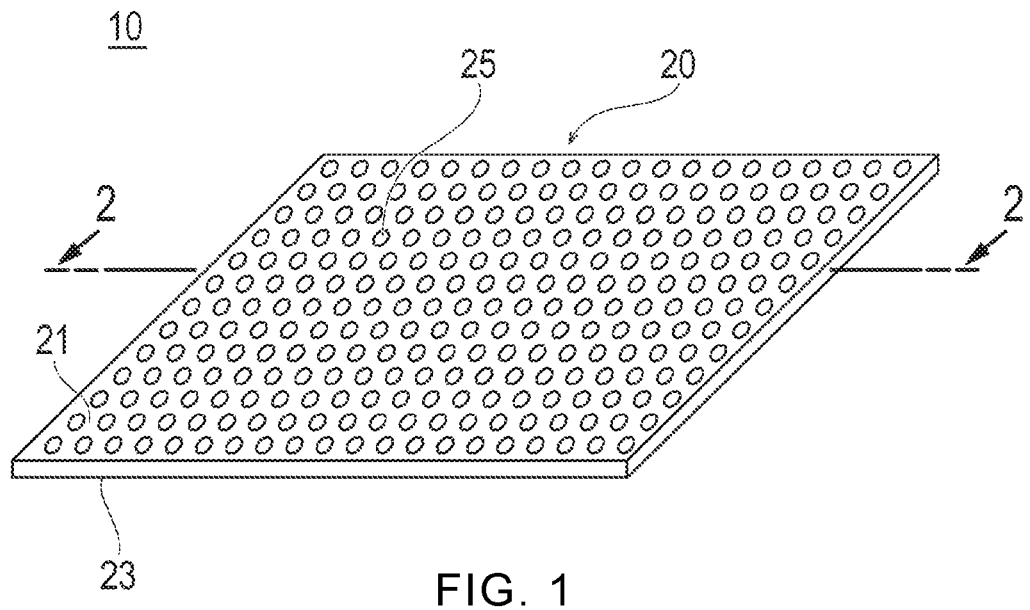
FIG. 1 is a perspective view illustrating a form of a medical device which can be used for a treatment method according to the present disclosure.
Figure 2:
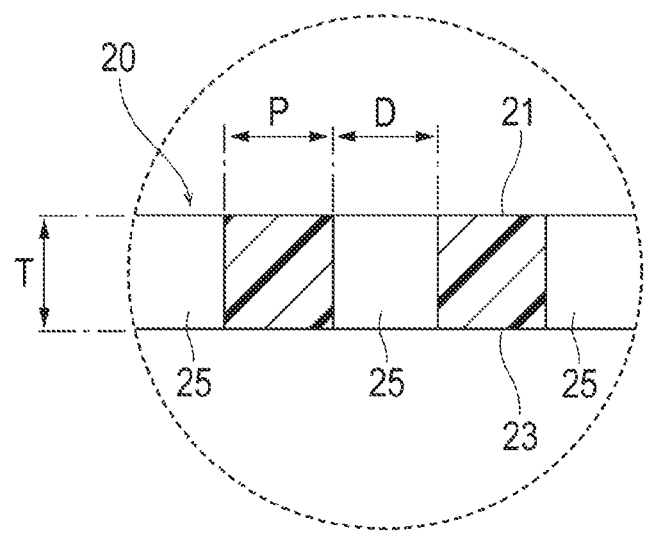
FIG. 2 is a partial detail section view illustrating a portion of a cross-section taken along line 2-2 illustrated in FIG. 1.

In FIG. 1, a perspective view illustrates a form of a medical device 10. FIG. 2 illustrates a section view taken along arrow line 2-2 illustrated in FIG. 1.

As illustrated in FIG. 1, the medical device 10 may be configured comprising a sheet-like (e.g., sheet-shaped, etc.) main body portion 20. For example, the main body portion 20 can be formed of a biodegradable sheet member (e.g., a thin film member, etc.).

The main body portion 20 may comprise a plurality of through-holes 25. As illustrated in FIG. 1, the plurality of through-holes 25 are regularly and repeatedly disposed in a plane direction of the main body portion 20. In some embodiments, the plurality of through-holes 25 may be randomly disposed in the main body portion 20.

As illustrated in FIG. 2, the plurality of through-holes 25 are vertically disposed along a thickness direction (e.g., an upward-downward direction as illustrated in FIG. 2) of the main body portion 20. The plurality of through-holes 25 are substantially vertically disposed between a front surface 21 and a rear surface 23 of the main body portion 20. However, the plurality of through-holes 25 may be disposed to be curved between the front surface 21 and the rear surface 23 in the thickness direction of the main body portion 20.

A thickness of the main body portion 20 (size T illustrated in FIG. 2) is not particularly limited. The thickness may be 0.05 mm to 0.3 mm, and in some embodiments may be 0.1 mm to 0.2 mm. Providing a thickness of the main body portion 20 of 0.05 mm or thicker (especially when the thickness is 0.1 mm or thicker), ensures sufficient strength of the main body portion 20 such that the main body portion 20 is not damaged when the medical device 10 is handled. On the other hand, providing a thickness of the main body portion 20 of 0.3 mm or thinner (particularly when the thickness is formed to be 0.2 mm or thinner), the main body portion 20 closely adheres to a biological tissue to which the main body portion 20 is applied, and it is possible to ensure sufficient flexibility to follow the biological tissue (e.g., by conforming to the shape and contour of the biological tissue, etc.).

As illustrated in FIG. 1, the main body portion 20 may comprise a substantially rectangular shape when observed in plan view. However, an outer shape of the main body portion 20 is not so limited, and may be circular or elliptical in shape, for example.

In the main body portion 20, a ratio value of a hole diameter D (distance D illustrated in FIG. 2) of the plurality of through-holes 25 to a pitch P (distance P illustrated in FIG. 2) of the plurality of through-holes 25 may be 0.25 or greater, and the ratio value may be smaller than 40. In some embodiments, a shape of the through-hole 25 when observed in plan view may correspond to a perfect circle and, as such, the hole diameter D of the through-hole 25 may be a diameter of a perfect circle. In one embodiment, the shape of the through-hole 25 when observed in plan view may not be a perfect circle, and a diameter (e.g., an equivalent circle diameter) of a perfect circle having an area the same as an area of an opening portion (portion facing the front surface 21 or the rear surface 23 in the through-hole 25) of the through-hole 25 can be set as the hole diameter D of the through-hole 25.

In addition, the main body portion 20 may include the plurality of through-holes 25. Therefore, the main body portion may have a plurality of values of the hole diameters D corresponding to the respective through-holes 25. In the present embodiment, in calculating the above-described ratio value, an arithmetic average value of two or more points of the value of the hole diameter D corresponding to each of the plurality of through-holes 25 is used as a representative value of the hole diameter D. In some embodiments, the "pitch P" of the through-holes 25 may correspond to the shortest distance between the opening portions of two adjacent through-holes 25. With regard to the value of the pitch P, there are a plurality of values of the pitch P corresponding to a combination of the through-holes 25 adjacent to each other. Therefore, according to embodiments of the present disclosure, in calculating the above-described ratio value, the arithmetic average value of two or more points of the value of the pitch P corresponding to each combination of the through-holes 25 adjacent to each other may be used as a representative value of the pitch P.

The pitch P of the above-described through-hole 25, the hole diameter D, and the ratio of the hole diameter D to the pitch P are merely provided as examples, and the present disclosure should not be limited thereto.

The main body portion 20 can be formed of a biodegradable material. A configuration material of the main body portion 20 is not particularly limited. For example, the configuration material may include a biodegradable resin. In some embodiments the biodegradable resin may, for example, be a known biodegradable (co) polymer such as those disclosed in Japanese Patent Application JP-T-2011-528275, Japanese Patent Application JP-T-2008-514719, Pamphlet of International Publication No. 2008-1952, and Japanese Patent Application JP-T-2004-509205, the entire contents of which are hereby incorporated herein by reference for all that they teach and for all purposes. Specifically, the biodegradable resin may include (1) a polymer selected from a group formed of aliphatic polyester, polyester, polyanhydride, polyorthoester, polycarbonate, polyphosphazene, polyphosphate ester, polyvinyl alcohol, polypeptide, polysaccharide, protein, and/or cellulose; or (2) a copolymer configured to include one or more monomers making up the above-described materials. In some embodiments, the biodegradable sheet may include the polymer selected from a group formed of aliphatic polyester, polyester, polyanhydride, polyorthoester, polycarbonate, polyphosphazene, polyphosphate ester, polyvinyl alcohol, polypeptide, polysaccharide, protein, and cellulose, and at least one biodegradable resin selected from a group formed of the copolymer configured to include one or more monomers making up the polymer.

A manufacturing method of the main body portion 20 is not particularly limited. For example, the manufacturing method can include a method of preparing a fiber formed of the above-described biodegradable resin and manufacturing a mesh-shaped sheet using the fiber. A method of preparing the fiber formed of the biodegradable resin is not particularly limited. For example, the method may include an electro-spinning method (e.g., electric field spinning method, electrostatic spinning method, or other fiber production method) or a melt blowing method. In producing the main body portion 20, any one of the above-described methods may be selected and used. Alternatively, two or more methods of manufacturing may be used in appropriate combination with each other to produce the main body portion 20. As yet another example of a manufacturing method for forming the main body portion 20, a fiber formed of the above-described biodegradable resin may be spun, and the obtained fiber may be knitted into a mesh shape to manufacture the biodegradable sheet according to the present disclosure.

The main body portion 20, when placed in contact with biological tissue, etc., causes a biological reaction to occur. In particular, the configuration materials, such as the biodegradable resin of the main body portion 20, may induce an expression of biological components, such as fibrin, from the biological tissue in contact with the main body portion 20. The biological components induced in this way can promote adhesion between separate joint target sites by being accumulated to penetrate the through-holes 25 of the main body portion 20 and join together. For example, the main body portion 20 of the medical device 10 may be placed between the biological organs to be joined (anastomosis objects), thereby promoting the adhesion by using the above-described mechanism.

Next, embodiments of a medical device will be described. The configuration, arrangement, and/or description provided in conjunction with the medical device 10 above may apply to the embodiments of the medical devices that follow. Accordingly, and for the sake of clarity, the content previously provided in conjunction with the medical device 10 above will be omitted in the description of the various embodiments of the medical device that follows.

Figure 3:
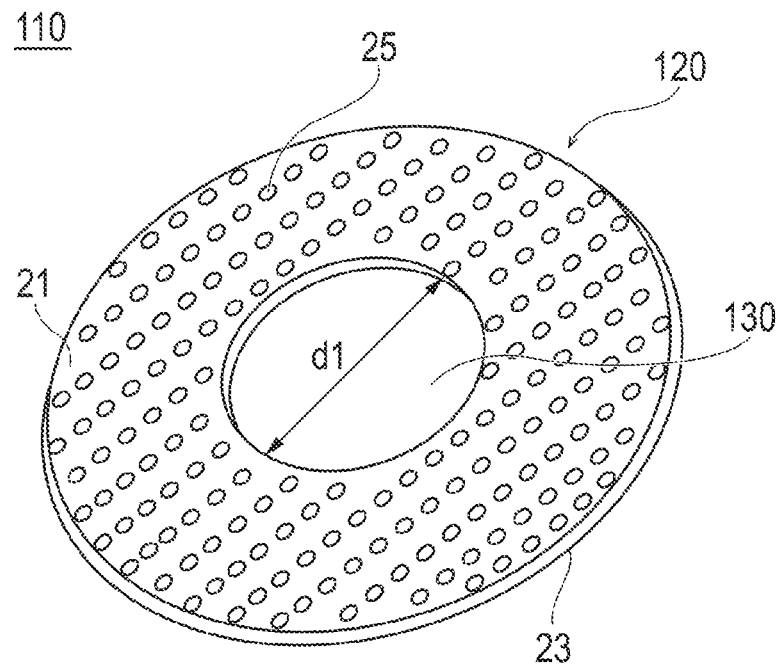
FIG. 3 is a perspective view illustrating an embodiment of a medical device which can be used for a treatment method according to the present disclosure.

FIG. 3 illustrates a perspective view of an embodiment of a medical device 110 according to the present disclosure.

As illustrated in FIG. 3, an embodiment of a medical device 110 may comprise a main body portion 120 having a circular shape when observed in plan view. The main body portion 120 may include a hole portion (e.g., a center hole) 130 having a hole diameter d1 that is larger than the diameter of each through-hole 25. The hole portion 130 may be disposed at a substantially central position (e.g., an approximate center) of the main body portion 120 when observed in plan view.

For example, a hole diameter d1 of the hole portion 130 can be formed to be 5 mm to 25 mm. In some embodiments, an outer shape of the hole portion 130 can be a perfect circle, for example. In one embodiment, the hole portion 130 may have an elliptical shape, a rectangular shape, or any other shape or combination of shapes.

Figure 4:
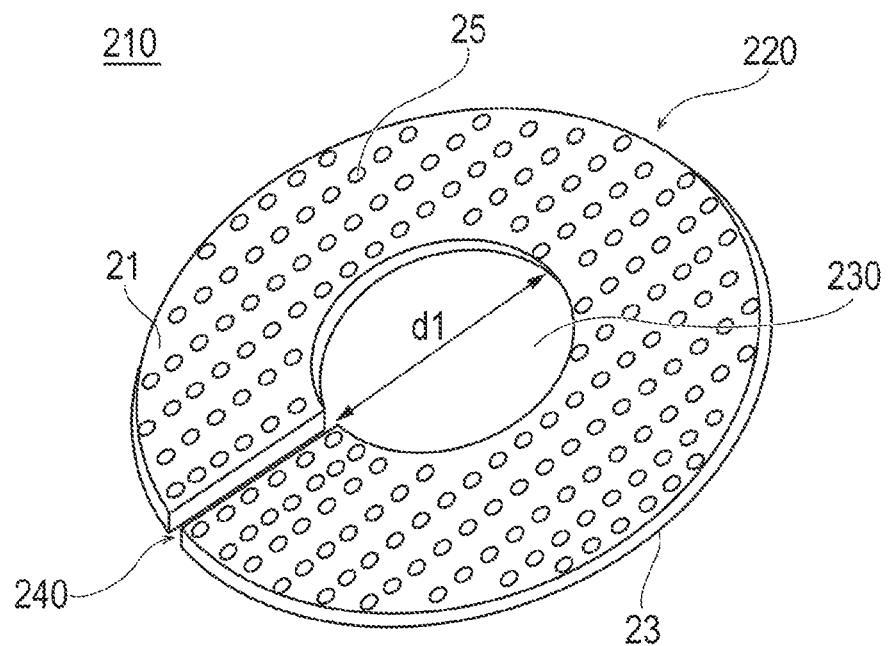
FIG. 4 is a perspective view illustrating an embodiment of a medical device which can be used for a treatment method according to the present disclosure.

FIG. 4 illustrates a perspective view of an embodiment of a medical device 210 according to the present disclosure.

As illustrated in FIG. 4, an embodiment of the medical device 210 may comprise a main body portion 220 having a circular shape when observed in plan view. The main body portion 220 may include a hole portion 230 formed to have a hole diameter d1 larger than the diameter of each through-hole 25. The hole portion 230 may be disposed at a substantially centered position (e.g., at an approximate center) of the main body portion 220 when observed in plan view. In some embodiments, the main body portion 220 may have a slit 240 (e.g., a slot, cut, void, etc.) running from a side surface (e.g., a periphery) of the main body portion 220 to a surface of the hole portion 230.

For example, the hole diameter d1 of the hole portion 230 can be formed to be 1 mm to 20 mm. In some embodiments, the shape of the slit 240 can be formed in a straight line shape when observed in plan view. However, a shape in which a curve or a straight line meanders, undulates, or otherwise deviates along a length of the slit 240 (e.g., a zigzag shape) may be employed without departing from the scope of the present disclosure.

Figure 5:
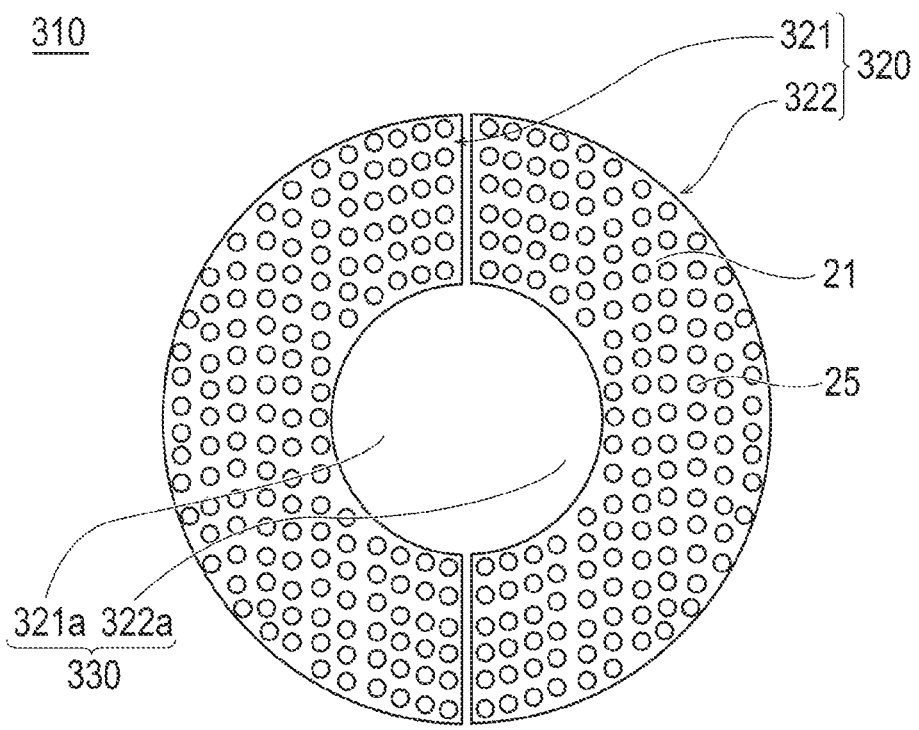
FIG. 5 is a plan view illustrating an embodiment of a medical device which can be used for a treatment method according to the present disclosure.

FIG. 5 illustrates a plan view of an embodiment of a medical device 310 according to the present disclosure.

As illustrated in FIG. 5, the medical device 310 may comprise a main body portion 320 including a first split piece 321 and a second split piece 322. The first split piece 321 and the second split piece 322 are formed by splitting the main body portion 320 in a radial direction to be substantially similar in shape. A concave portion 321a formed in the first split piece 321 and a concave portion 322a formed in the second split piece 322 form a space 330 corresponding to a hole portion at a substantially center position of the main body portion 320, when the first split piece 321 and the second split piece 322 are arranged side by side.

Although shown split into two pieces 321, 322, the main body portion 320 may be split, or separated, into any number of split pieces. Additionally or alternatively, the shape of the respective split pieces is not limited to half sections as shown in FIG. 5, and may be changed to suit a particular treatment method or area of treatment.

Figure 6:
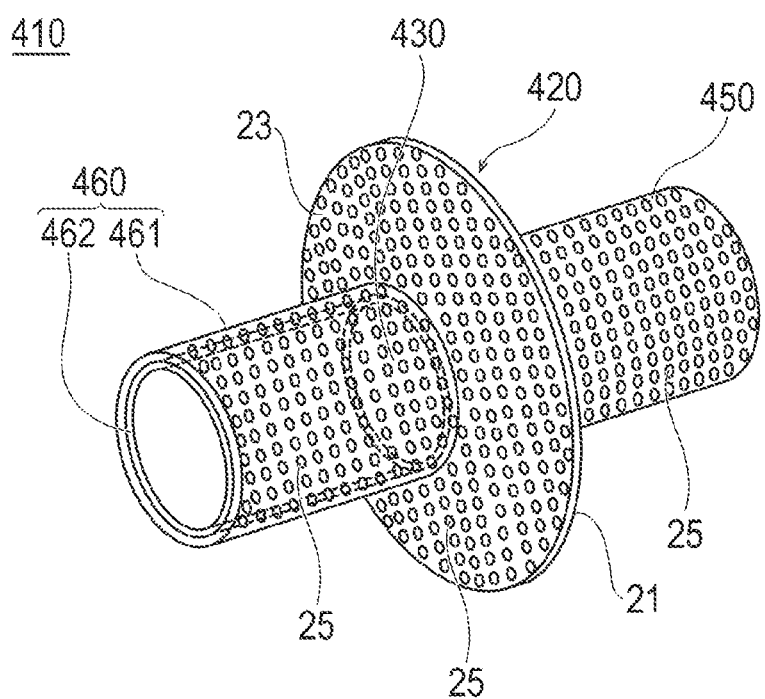
FIG. 6 is a perspective view illustrating an embodiment of a medical device which can be used for a treatment method according to the present disclosure.

FIG. 6 illustrates an embodiment of a medical device 410 according to the present disclosure.

As illustrated in FIG. 6, the medical device 410 may comprise a sheet-like main body portion 420 having a hole portion 430, a hollow first tubular portion 450 protruding from the front surface 21 side of the main body portion 420, and a hollow second tubular portion 460 protruding from the rear surface 23 side of the main body portion 420.

The first tubular portion 450 and the second tubular portion 460 may communicate with each other via the hole portion 430 of the main body portion 420.

For example, the first tubular portion 450 can be formed of a material the same as that of the main body portion 420 (material the same as that of the main body portion 20 described above). The first tubular portion 450 internally may comprise a lumen through which a fluid can be circulated or otherwise conveyed. In addition, the first tubular portion 450 may include through-holes 25 disposed around a periphery thereof.

The second tubular portion 460 may comprise a substantially cylindrical outer member 461 having through-holes 25 disposed therein and a substantially cylindrical inner member 462 placed on an inner surface of the outer member 461.

The outer member 461 and the inner member 462 may be formed of a material the same as that of the main body portion 420. In some embodiments, the through-holes 25 may not be formed in the inner member 462. The inner member 462 internally may comprise a lumen through which a fluid such as a body fluid can be circulated or otherwise conveyed.

Figure 7:
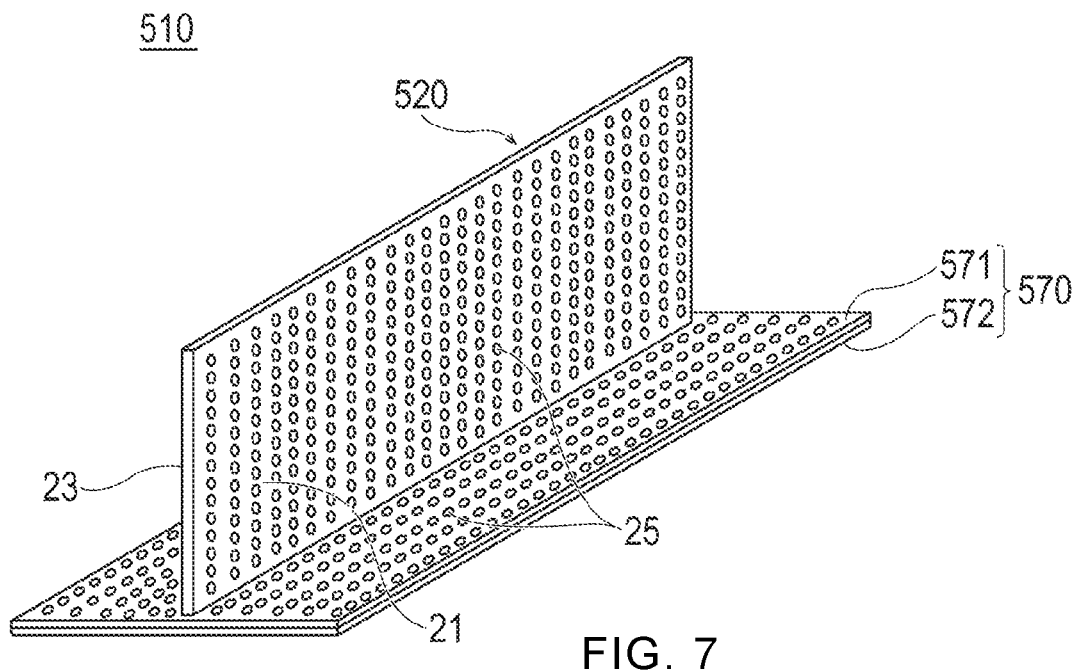
FIG. 7 is a perspective view illustrating an embodiment of a medical device which can be used for a treatment method according to the present disclosure.

FIG. 7 illustrates a perspective view of an embodiment of a medical device 510 according to the present disclosure.

As illustrated in FIG. 7, the medical device 510 may comprise a sheet-like main body portion 520 and a guide portion 570.

The main body portion 520 may comprise a substantially rectangular shape when observed in plan view. The guide portion 570 may be disposed to be substantially perpendicular to a plane direction of the main body portion 520.

The guide portion 570 may comprise a first sheet member 571 having the through-holes 25 disposed therein and a second sheet member 572 placed in contact with and overlapping at least a portion of the first sheet member 571. The through-holes 25 may not be formed in the second sheet member 572.

For example, the second sheet member 572 can be configured to be more rigid (e.g., having a harder physical property) than the first sheet member 571. As an example, the first sheet member 571 and the second sheet member 572 may be formed of a material which is the same as that of the main body portion 520, and the through-holes 25 may be formed in the first sheet member 571. In this manner, a rigidity magnitude relationship between the first sheet member 571 and the second sheet member 572 can be adjusted.

Figure 8:
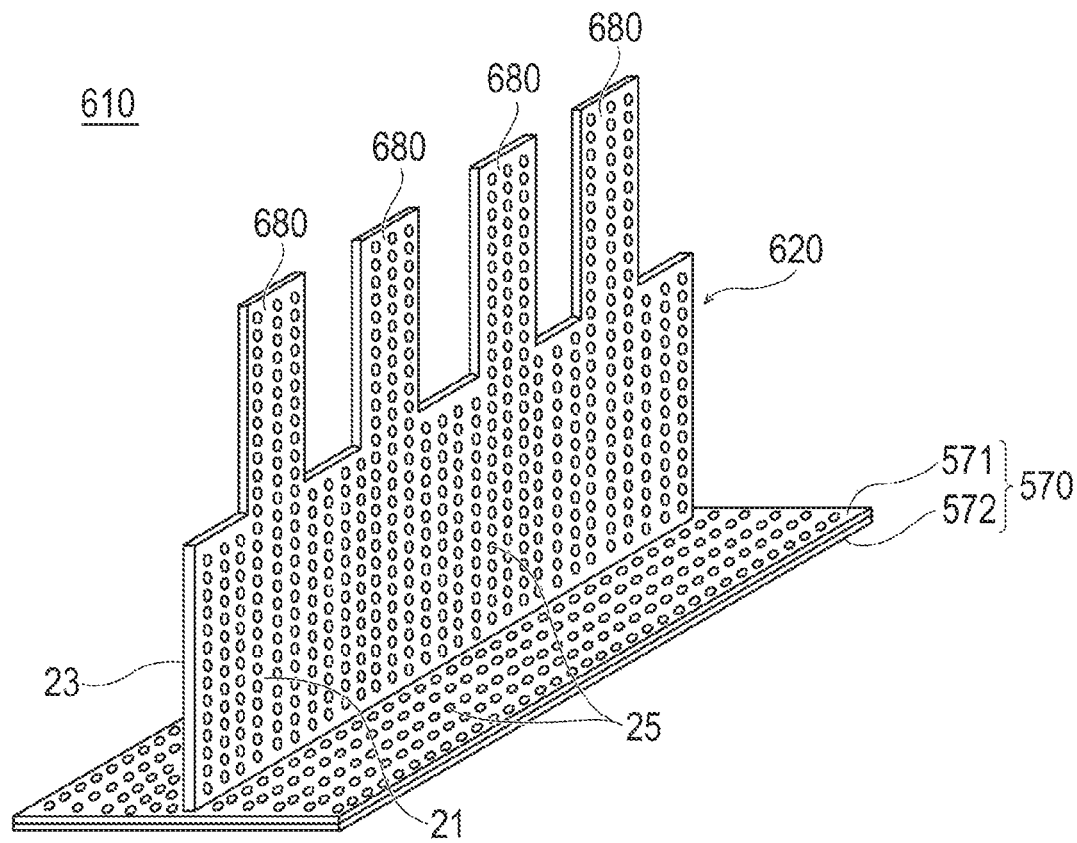
FIG. 8 is a perspective view illustrating an embodiment of a medical device which can be used for a treatment method according to the present disclosure.

FIG. 8 illustrates a perspective view of an embodiment of a medical device 610 according to the present disclosure.

As illustrated in FIG. 8, the medical device 610 may comprise a sheet-like main body portion 620, the guide portion 570, and a protruding portion 680 protruding from one side (side surface) of the main body portion 620. The main body portion 620 and the guide portion 570 can be formed in the same manner as described in conjunction with the medical device 510 above.

For example, as illustrated in FIG. 8, four of the protruding portions 680 can be disposed on one side surface of the main body portion 620. A shape of the protruding portion 680, a length in a protruding direction, a width in a direction intersecting the protruding direction, a pitch between the protruding portions 680, and the number of the protruding portions 680 are not limited to those shown in FIG. 8. For example, in a case where the medical device 610 may be used for anastomosis of an esophagus-gastric tube, the medical device 610 can include any desired number of the protruding portions 680, depending on the number of support sutures adopted for the medical procedure.

The embodiments described above provide a number of examples of the medical device for explanation purposes. The scope of the embodiments herein are not intended to be limited to those embodiments described above. Each of the embodiments of the medical devices described above can be used in conjunction with the treatment methods according to the present disclosure and comprise a sheet-like main body portion that promotes the adhesion of biological tissues. For example, as another embodiment, the medical device may have a communication hole exposed on a side surface of the main body portion. Additionally or alternatively, the medical device may have a shape in which a portion of the through-hole formed in the main body portion is widened in a direction intersecting a thickness direction (e.g., the upward-downward direction in FIG. 2) of the main body portion. Additionally or alternatively, the medical device may have a shape in which a portion of the through-hole formed in the main body portion is narrowed in the direction intersecting the thickness direction (e.g., the upward-downward direction in FIG. 2) of the main body portion.

Next, a treatment method according to embodiments of the present disclosure will be described.

Figure 9:
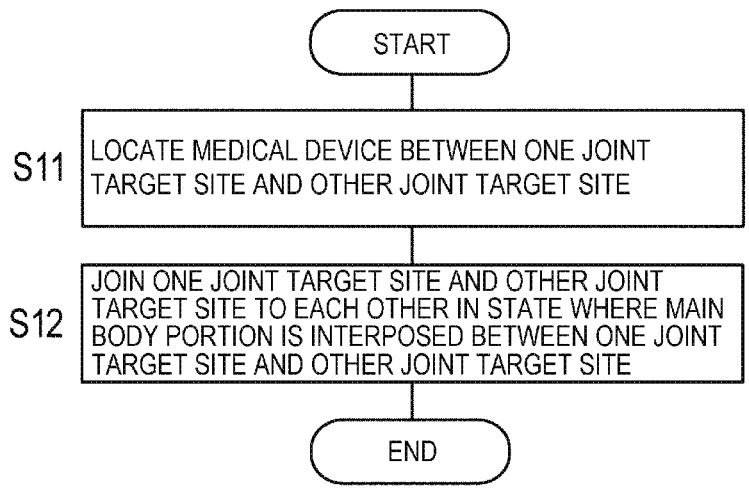
FIG. 9 is a flowchart illustrating a treatment method in accordance with embodiments of the present disclosure.

FIG. 9 is a flowchart illustrating a treatment method according to the present disclosure.

The treatment method according to the present disclosure may comprise placing a sheet-like main body portion for promoting the adhesion of the biological tissues between one joint target site (e.g., a first joint target site) and another joint target site (e.g., a second joint target site) of the biological organ to be joined (S11), and joining the first joint target site and the second joint target site in a state where at least a portion of the main body portion of the medical device is placed between the first joint target site and the second joint target site (S12).

The biological organ and the joint target site in the biological organ which are joined by using the treatment method according to the present disclosure are not limited to the sites of the several examples described, and can include any biological sites that are to be joined together. However, in the following description, examples will be described in which the treatment method according to the present disclosure is applied to (i) large intestine anastomosis, (ii) pancreatic parenchyma-jejunum anastomosis, and (iii) esophagus-gastric tube anastomosis. It is possible to select any desired embodiment of the medical device at least from the above-described respective medical devices 10, 210, 310, 410, 510, and 610, and it is also possible to select other medical devices as described, or contemplated, herein. In the following description, a specific embodiment of a medical device may be described in conjunction with representative example medical procedures. In each medical procedure described below, the detailed description of known medical procedures, known medical devices, and/or known medical instruments will be omitted for clarity.

As described herein, the term "placing the medical device between the biological organs" may mean at least any one of placing the medical device in a state of being in a direct or indirect contact with the biological organs, placing the medical device in a state where a spatial gap is formed between the biological organs, and/or placing the medical device in both the states (for example, placing the medical device in a state where the medical device is in contact with one biological organ and the medical device is not in contact with the other biological organ). In addition, in the description herein, a "periphery" does not define a strict range (region), and may correspond to a predetermined range (region) as long as an objective of the disclosure can be achieved (e.g., joining the biological organs to each other). In addition, as long as the objective of the disclosure can be achieved, in the medical procedure described in the respective treatment methods, orders of steps described may be rearranged or otherwise performed out of the sequences described. As described herein, "moving two portions relatively closer to each other" means both moving two or more objects closer to each other, and/or moving only one portion closer to the other one (e.g., without moving the other one, etc.).

Figure 10:
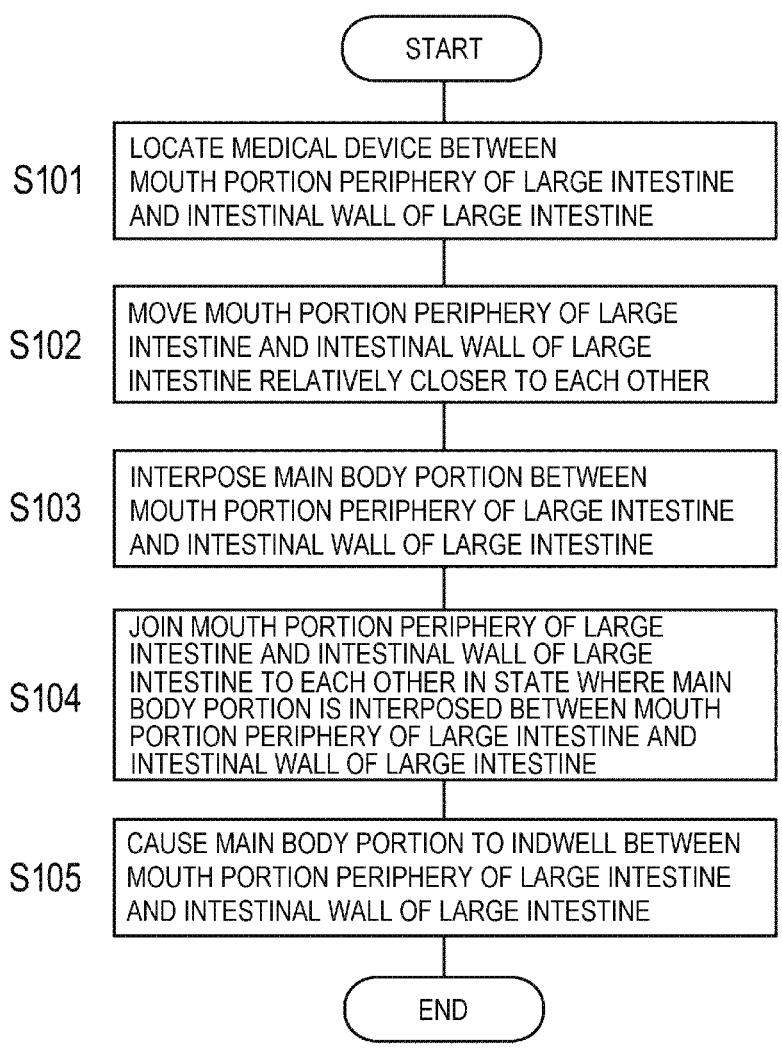
FIG. 10 is a flowchart illustrating a treatment method according to a first embodiment of the present disclosure.
Figure 11:
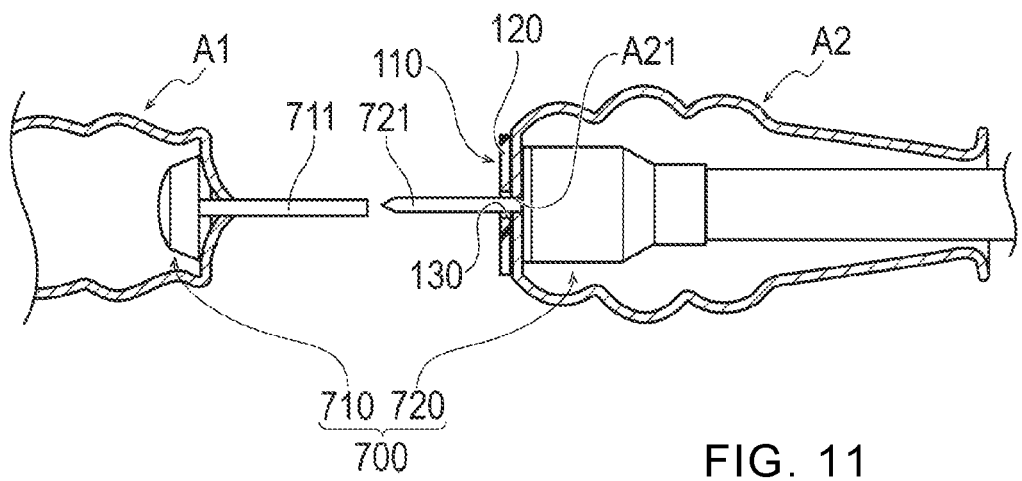
FIG. 11 is a schematic section view illustrating a state of a treatment method according to a first embodiment of the present disclosure.
Figure 12:
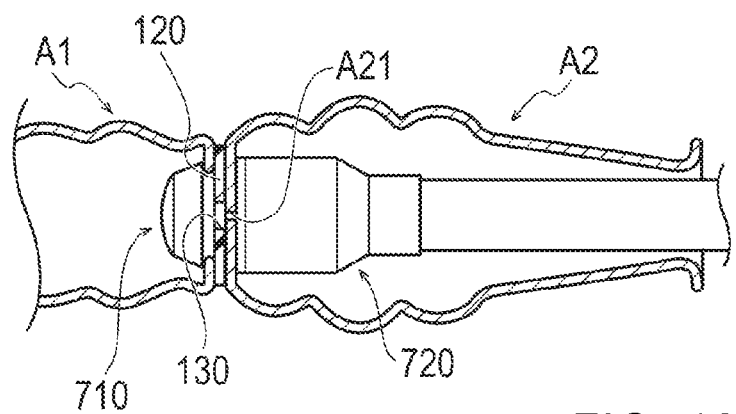
FIG. 12 is a schematic section view illustrating a state of the treatment method according to the first embodiment.
Figure 13:
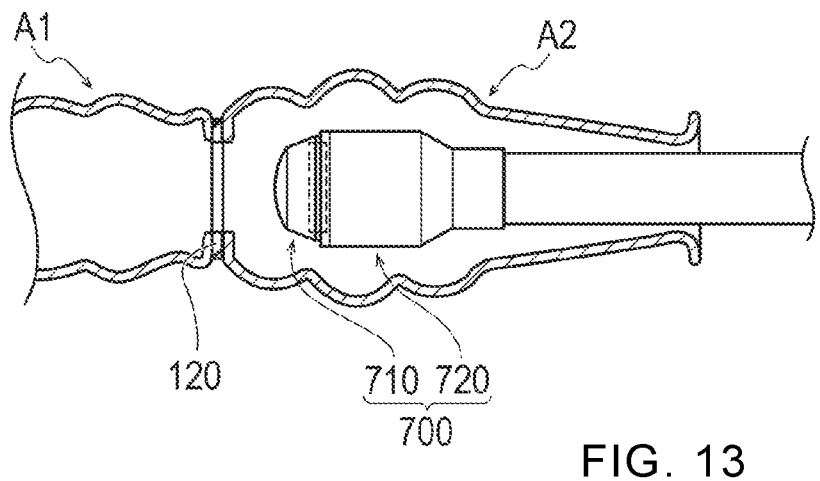
FIG. 13 is a schematic section view illustrating a state of the treatment method according to the first embodiment.

FIG. 10 is a flowchart illustrating a procedure of large intestine anastomosis according to a first embodiment of the present disclosure. FIGS. 11 to 13 are views illustrating various states associated with the treatment method (e.g., the procedure of large intestine anastomosis) according to the first embodiment.

In the treatment method according to the present embodiment, the biological organ to be joined may be a large intestine cut, for example, due to excision of a cancer tumor or other foreign object. Specifically, the biological organs to be joined are a cut mouth side of the large intestine A1 and a cut anal side of the large intestine A2. A procedure for joining a mouth portion periphery (a first joint target site) of the cut mouth side of the large intestine A1 to a portion of an intestinal wall of the cut anal side of the large intestine A2 (the second joint target site) is described herein. By way of example, the present treatment method will be described using the medical device 110 of FIG. 3.

As illustrated in FIG. 10, the treatment method according to the present embodiment may include placing the medical device between the mouth portion periphery of the large intestine and the intestinal wall of the large intestine (S101), moving the mouth portion periphery of the large intestine and the intestinal wall of the large intestine to relatively closer to each other (S102), interposing the main body portion of the medical device between the mouth portion periphery of the large intestine and the intestinal wall of the large intestine (S103), joining both of these to each other in a state where the main body portion of the medical device is interposed between the mouth portion periphery of the large intestine and the intestinal wall of the large intestine (S104), and causing the main body portion of the medical device to indwell between the mouth portion periphery of the large intestine and the intestinal wall of the large intestine (S105).

Next, referring to FIGS. 11 to 13, the treatment method according to the present embodiment will be described in detail.

As illustrated in FIG. 11, an operator such as a doctor (hereinafter, referred to as an operator) inserts a first engagement instrument 710 of an anastomosis device 700 into the mouth side of the large intestine A1. The operator places a second engagement instrument 720 of the anastomosis device 700 on the anal side of the large intestine A2. Before the second engagement instrument 720 is placed on the anal side of the large intestine A2, the operator forms a through-hole A21 for inserting the second engagement instrument 720 of the anastomosis device 700 into the anal side of the large intestine A2. A timing at which the through-hole A21 is formed is not particularly limited as long as the timing is before the second engagement instrument 720 is placed.

For example, an anastomosis device 700 may be used for the large intestine anastomosis procedure described herein As the first engagement instrument 710 and the second engagement instrument 720 engage with each other, the anastomosis device 700 excises the biological tissue between the first engagement instrument 710 and the second engagement instrument 720, and sutures a periphery of the excised biological tissue into a circumferential shape, for instance, by using a stapler. For example, the first engagement instrument 710 may be an instrument including a cylindrical engagement target portion 711. The second engagement instrument 720 may be an instrument including an engagement pin 721 configured to engage with and be inserted into the engagement target portion 711 of the first engagement instrument 710.

Next, as illustrated in FIG. 11, the operator places the medical device 110 between the mouth side of the large intestine A1 and the anal side of the large intestine A2. According to the present embodiment, the medical device 110 (refer to FIG. 3) where the hole portion (center hole) 130 is formed in the main body portion 120 is used. When the operator places the medical device 110, the operator causes the engagement pin 721 included in the second engagement instrument 720 to pass through the hole portion 130 formed in the main body portion 120. In this case, the operator brings the main body portion 120 of the medical device 110 into contact with the vicinity having the through-hole A21 formed on the anal side of the large intestine A2. The operator may place the medical device 110 on the mouth side of the large intestine A1 by causing the engagement target portion 711 included in the first engagement instrument 710 to pass through the hole portion 130 formed in the main body portion 120.

Next, as illustrated in FIG. 12, the operator engages the first engagement instrument 710 and the second engagement instrument 720 with each other by moving both of these instruments 710, 720 relatively closer to each other. The operator interposes the mouth portion periphery on the mouth side of the large intestine A1, the main body portion 120 of the medical device 110, the periphery of the through-hole A21 formed on the intestinal wall on the anal side of the large intestine A2 between the first engagement instrument 710 and the second engagement instrument 720. The operator operates the anastomosis device 700. In this manner, while the operator incises a portion on the mouth side of the large intestine A1, a portion of the main body portion 120 of the medical device 110, and a portion on the anal side of the large intestine A2 interposed between the first engagement instrument 710 and the second engagement instrument 720, the operator joins the peripheries of the cut portions to each other by, for instance, using a stapler (not illustrated).

Next, as illustrated in FIG. 13, the operator removes the anastomosis device 700 outward of the living body from the anal side of the large intestine A2 via the anus, for example. In addition, the operator causes the medical device 110 to indwell in a state where a portion of the main body portion 120 of the medical device 110 is interposed between the mouth portion periphery on the mouth side of the large intestine A1 and the intestinal wall of the anal side of the large intestine A2.

As described above, the treatment method according to the present embodiment is applicable to the medical procedure for joining the large intestine. In the treatment method according to the present embodiment, the mouth portion periphery of the large intestine and the intestinal wall of the large intestine are joined to each other. According to the treatment method, the main body portion 120 of the medical device 110 placed between the mouth portion periphery on the mouth side of the large intestine A1 and the intestinal wall on the anal side of the large intestine A2 promotes the adhesion between the biological tissue in the periphery on the mouth side of the large intestine A1 and the biological tissue on the intestinal wall on the anal side of the large intestine A2. Among other things, this promoted adhesion provides a completely sealed continuous joint, at a surface area, between the biological tissues reducing the risk factors that contribute to anastomotic leakage after large intestine anastomosis is performed.

In addition, the treatment method according to the present embodiment may include placing the first engagement instrument 710 of the anastomosis device 700 in the mouth portion of the large intestine, and placing the second engagement instrument 720 of the anastomosis device 700 in the through-hole A21 formed on the intestinal wall of the large intestine. Then, the main body portion 120 of the medical device 110 may comprise the hole portion 130 which enables the medical device 110 to be mounted on the first engagement instrument 710 or the second engagement instrument 720. The treatment method according to the present embodiment may comprise the following steps. In a state where the medical device 110 is mounted on the first engagement instrument 710 or the second engagement instrument 720, the mouth portion periphery of the large intestine and the intestinal wall of the large intestine may be moved relatively closer to each other. In this manner, the main body portion 120 of the medical device 110 is interposed between the mouth portion periphery of the large intestine and the intestinal wall of the large intestine. According to the above-described treatment method, in the large intestine anastomosis using the anastomosis device 700, each work can be easily and smoothly carried out in mounting the medical device 110 on the anastomosis device 700, in placing the medical device 110 in the joint target site, and in interposing the main body portion 120 of the medical device 110 between target sites.

Figure 14:
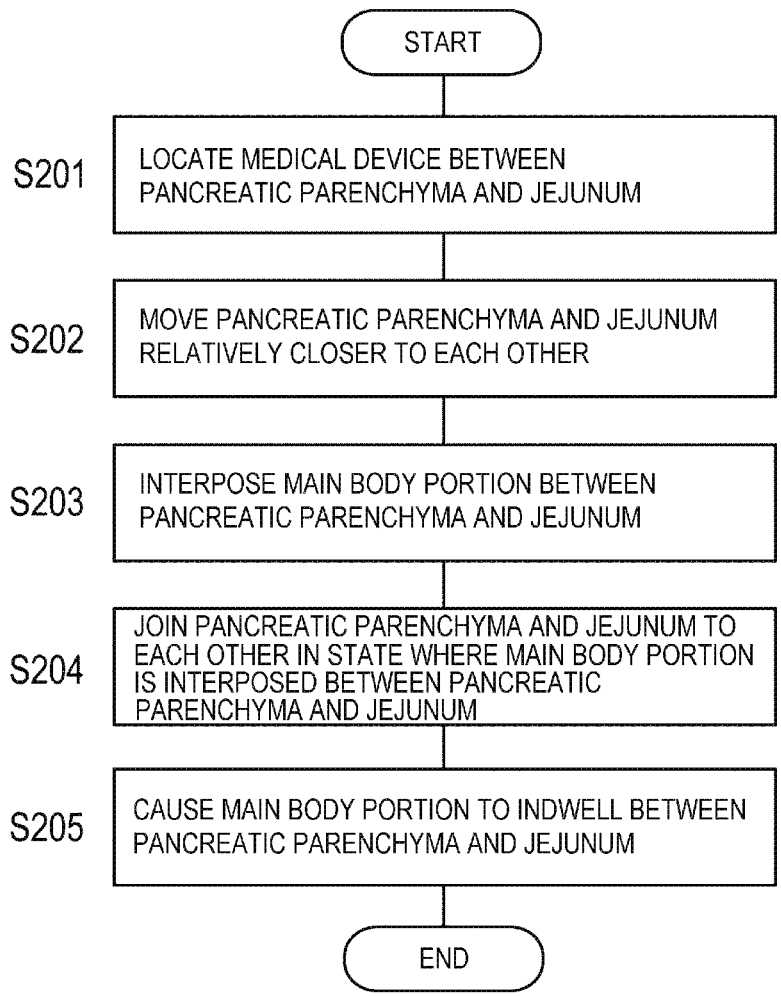
FIG. 14 is a flowchart illustrating a treatment method according to a second embodiment of the present disclosure.

FIG. 14 is a flowchart illustrating a procedure of pancreatic parenchyma-jejunum anastomosis according to a second embodiment of the present disclosure. FIGS. 15 to 24 are views illustrating various states associated with the treatment method (e.g., the procedure of pancreatic parenchyma-jejunum anastomosis) according to the second embodiment.

In the treatment method according to the present embodiment, the biological organs to be joined may be a pancreatic parenchyma B1 and a jejunum B2 after pancreaticoduodenectomy is performed. A procedure will be described in which a cut cross section periphery (a first joint target site) of the cut pancreatic parenchyma B1 and an optional site (the second joint target site) on the intestinal wall of the jejunum B2 are joined to each other. By way of example, the present treatment method will be described using the medical device 110 of FIG. 3.

As illustrated in FIG. 14, the treatment method according to the present embodiment may include placing the medical device between the pancreatic parenchyma and the jejunum (S201), moving the pancreatic parenchyma and the jejunum relatively closer to each other (S202), interposing the main body portion of the medical device between the pancreatic parenchyma and the jejunum (S203), joining both of these in a state where the main body portion of the medical device is interposed between the pancreatic parenchyma and the jejunum (S204), and causing the main body portion of the medical device to indwell between the pancreatic parenchyma and the jejunum (S205).

Next, referring to FIGS. 15 to 24, the treatment method according to the present embodiment will be described in detail.

Figure 15:
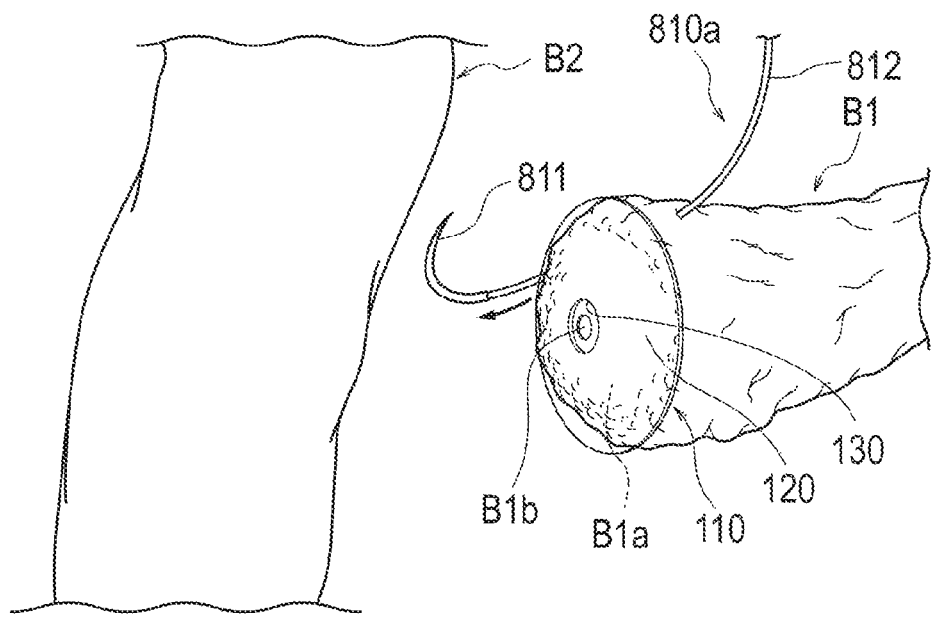
FIG. 15 is a schematic perspective view illustrating a state of a treatment method according to the second embodiment of the present disclosure.

As illustrated in FIG. 15, an operator places the main body portion 120 of the medical device 110 on a cut surface B1a of the cut pancreatic parenchyma B1. In this example, the operator places the hole portion 130 formed in the main body portion 120 to be aligned with an open end (portion facing an outer surface of the pancreatic parenchyma B1 in the pancreatic duct B1b) of the pancreatic duct B1b facing the cut surface B1a of the pancreatic parenchyma B1. In this way, the operator attaches the main body portion 120 of the medical device 110 to the cut surface B1a of the pancreatic parenchyma B1.

Next, as illustrated in FIG. 15, the operator operates a double end needle 810a from a front wall (portion on the front side in the circumferential direction of the pancreatic parenchyma B1) of the pancreatic parenchyma B1 toward a rear wall (portion on the rear side in the circumferential direction of the pancreatic parenchyma B1). As the double end needle 810a, it is possible to use a needle including a needle portion 811 provided with biocompatibility and an absorbable suture 812 provided with bioabsorbability. The needle portion 811 may be attached to both ends of the absorbable suture 812. The double end needles 810*b*, 810*c*, 810*d* (to be described later), may be the same as, or similar to, the double end needle 810*a* described above.

Figure 16:
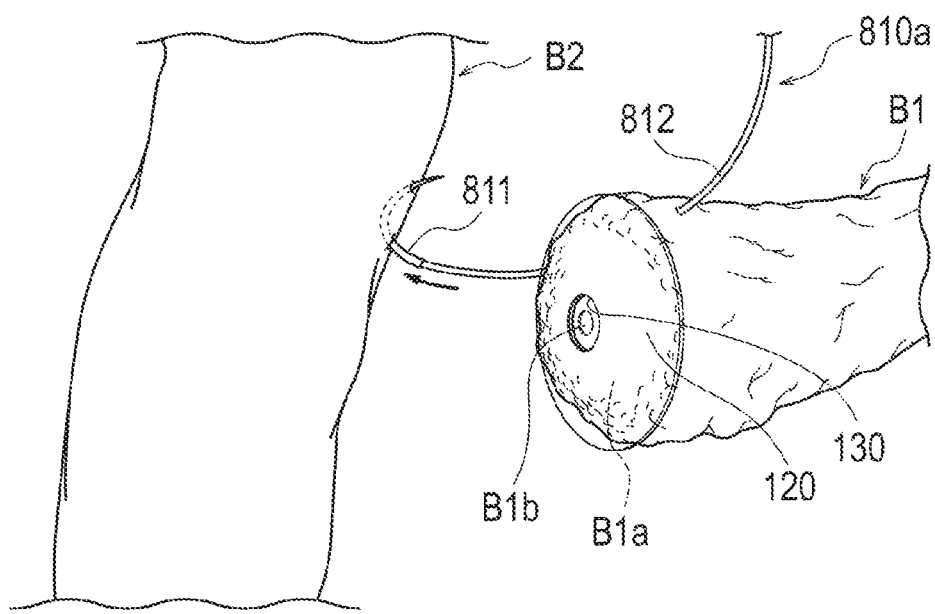
FIG. 16 is a schematic perspective view illustrating a state of the treatment method according to the second embodiment.

Next, as illustrated in FIG. 16, the operator operates the double end needle 810*a* so that the needle portion 811 passes through a jejunal serous muscle layer of the jejunum B2.

Figure 17:
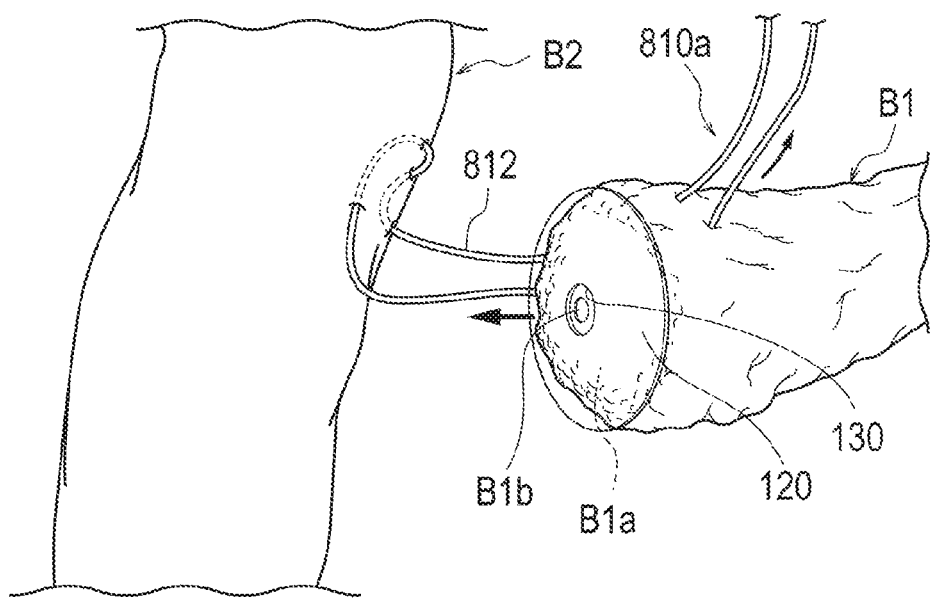
FIG. 17 is a schematic perspective view illustrating a state of the treatment method according to the second embodiment.

Next, as illustrated in FIG. 17, the operator operates the double end needle 810*a* to be folded from the jejunum B2 side to the pancreatic parenchyma B1 side, and causes the needle portion 811 to pass through a front wall of the pancreatic parenchyma B1 from a rear wall of the pancreatic parenchyma B1. In addition, while the operator operates the double end needle 810*a* as described above, the operator moves the pancreatic parenchyma B1 closer to the jejunum B2 side. In a state of adhering to the cut surface B1*a* of the pancreatic parenchyma B1, the main body portion 120 of the medical device 110 is interposed between the cut surface B1*a* of the pancreatic parenchyma B1 and the intestinal wall of the jejunum B2.

Figure 18:
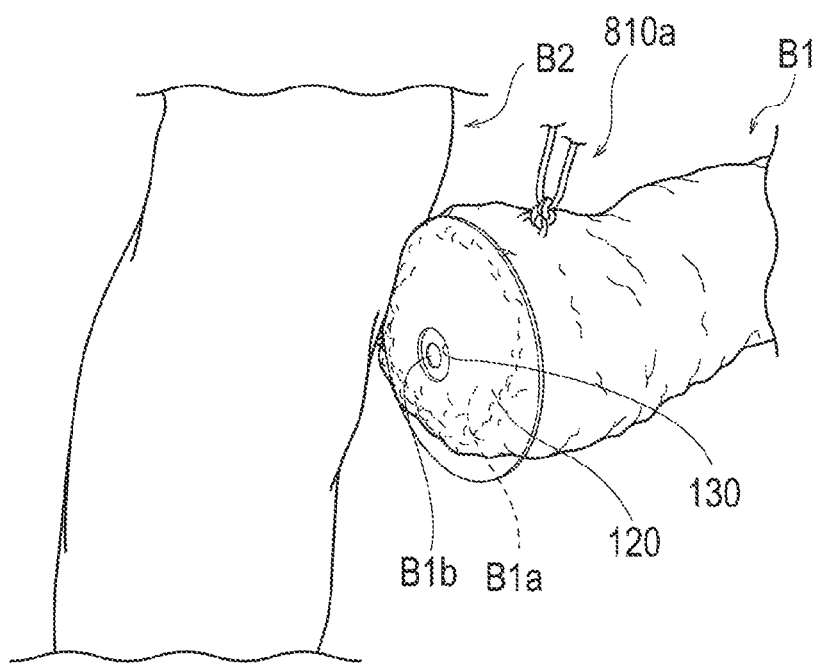
FIG. 18 is a schematic perspective view illustrating a state of the treatment method according to the second embodiment.

In some embodiments, the operator may then suture the rear wall of the pancreatic parenchyma B1, the jejunal serous muscle layer of the jejunum B2, and the main body portion 120 of the medical device 110 by using the double end needle 810*a*. Next, as illustrated in FIG. 18, the operator holds the double end needle 810*a* at a predetermined position by tying a knot in the absorbable suture 812 of the double end needle 810*a*.

Figure 19:
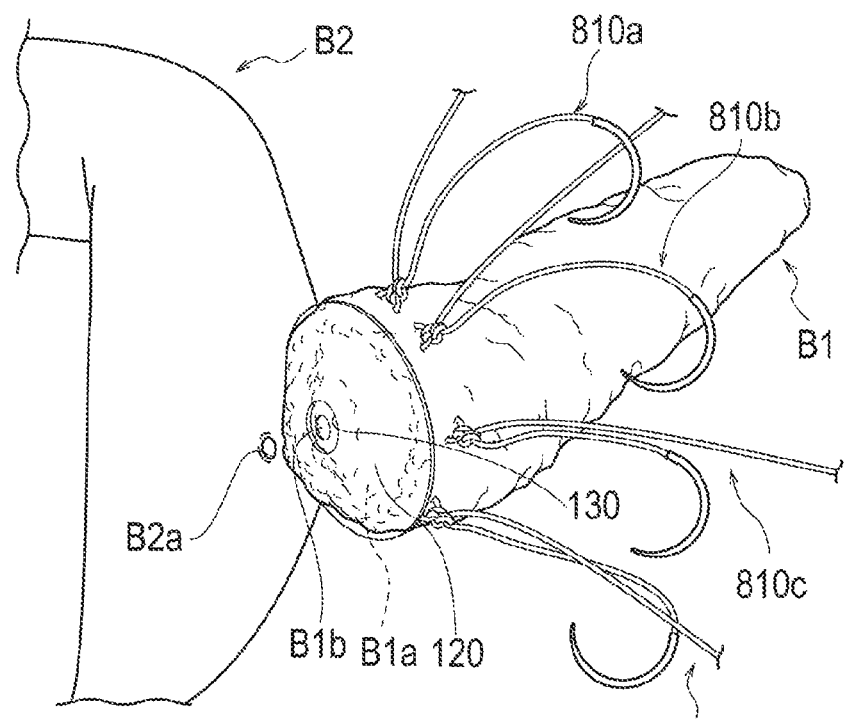
FIG. 19 is a schematic perspective view illustrating a state of the treatment method according to the second embodiment.

Next, as illustrated in FIG. 19, the operator uses the other double end needles 810*b*, 810*c*, and 810*d* repeats the steps described above for additional areas around a portion of the pancreatic parenchyma B1. The operator sutures the rear wall of the pancreatic parenchyma B1, the jejunum B2, and the main body portion 120 of the medical device 110, at three locations different from the location sewn by the double end needle 810*a*. After the rear wall of the pancreatic parenchyma B1 is completely sutured, the operator ties a knot in each absorbable suture of the respective double end needles 810*b*, 810*c*, and 810*d*, thereby holding the respective double end needles 810*b*, 810*c*, and 810*d* at predetermined positions. The operator carries out the above-described work. In this manner, as illustrated in FIG. 19, the operator may hang eight needles from the pancreatic parenchyma B1.

Next, as illustrated in FIG. 19, the operator forms a through-hole B2*a* penetrating an interior and an exterior of the jejunum B2 on a jejunum serosal surface of the jejunum B2.

Figure 20:
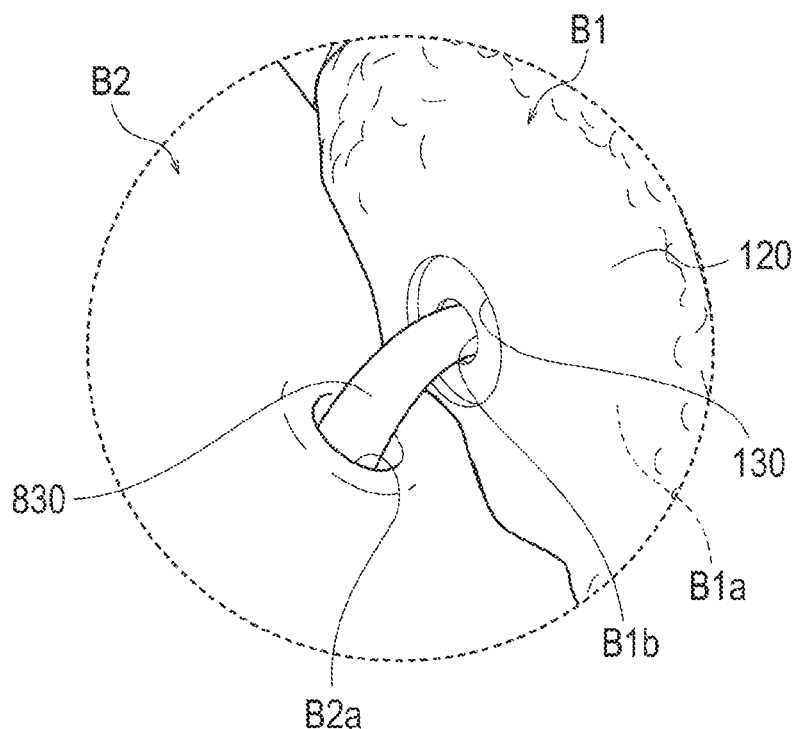
FIG. 20 is a partial detail perspective view illustrating a state of the treatment method according to the second embodiment.

Next, as illustrated in FIG. 20, the operator inserts a pancreatic duct tube 830 from the inner side of the jejunum B2. In addition, the operator inserts the pancreatic duct tube 830 into the pancreatic duct B1*b* by causing the pancreatic duct tube 830 to pass through the through-hole B2*a* formed in the jejunum B2. For example, as the pancreatic duct tube 830, it is possible to use a known resin-made tube in which a detachment preventing claw (convex portion) is formed on an end portion side to be inserted into the pancreatic duct B1*b*.

Figure 21:
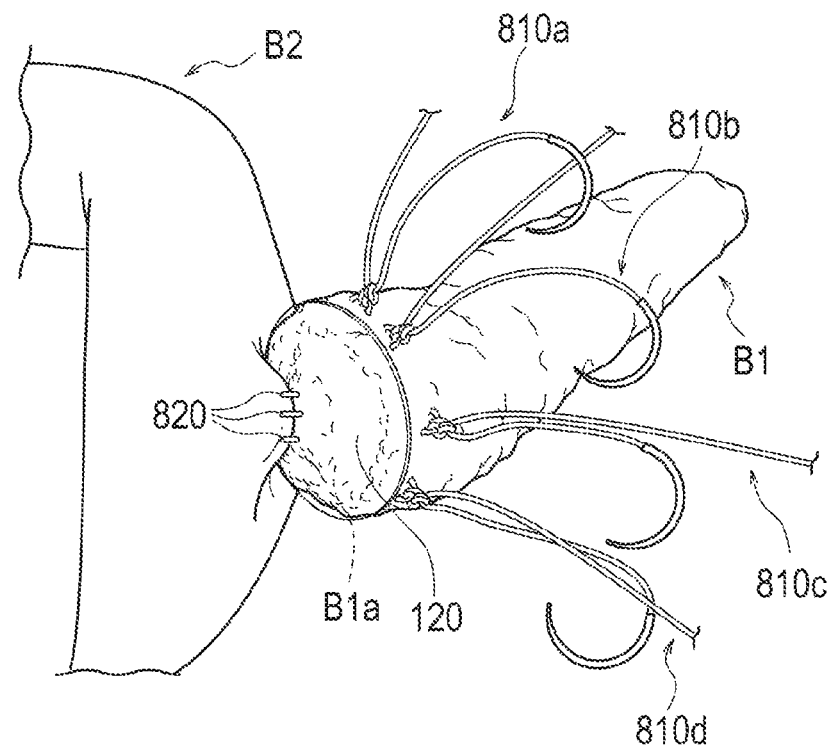
FIG. 21 is a schematic perspective view illustrating a state of the treatment method according to the second embodiment.

The operator inserts the pancreatic duct tube 830 into the pancreatic duct B1*b*, and aligns the pancreatic duct tube 830 with a predetermined position. Thereafter, as illustrated in FIG. 21, the operator uses a biodegradable suture 820, and sutures (fixes) the pancreatic duct tube 830 to the pancreatic duct B1*b*.

Figure 22:
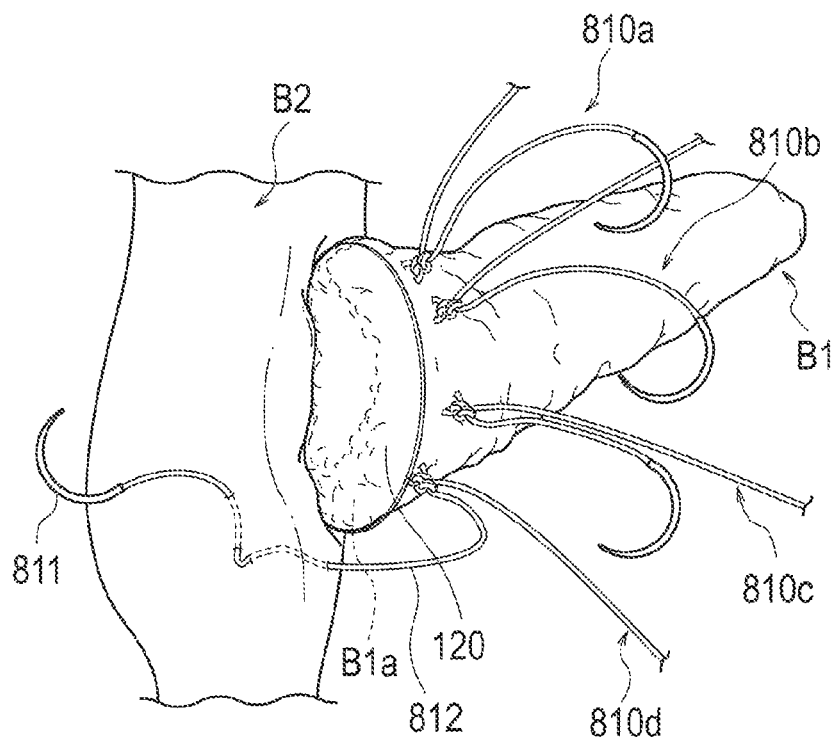
FIG. 22 is a schematic perspective view illustrating a state of the treatment method according to the second embodiment.
Figure 23:
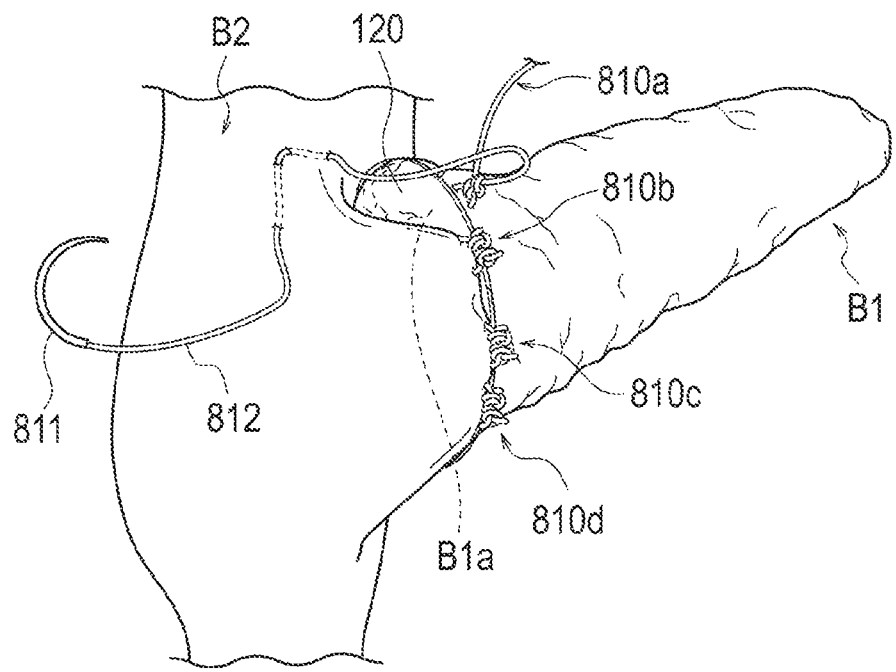
FIG. 23 is a schematic perspective view illustrating a state of the treatment method according to the second embodiment.

Next, as illustrated in FIGS. 22 and 23, the operator operates the respective double end needles 810*a*, 810*b*, 810*c*, and 810*d* held in the pancreatic parenchyma B1, and sutures the front wall of the pancreatic parenchyma B1, the jejunal serous muscle layer of the jejunum B2, and the main body portion 120 of the medical device 110. Due to tension generated when the suturing is performed, the jejunum B2 may be deformed to wrap around the cut surface B1*a* of the pancreatic parenchyma B1 and the main body portion 120 of the medical device 110.

Figure 24:
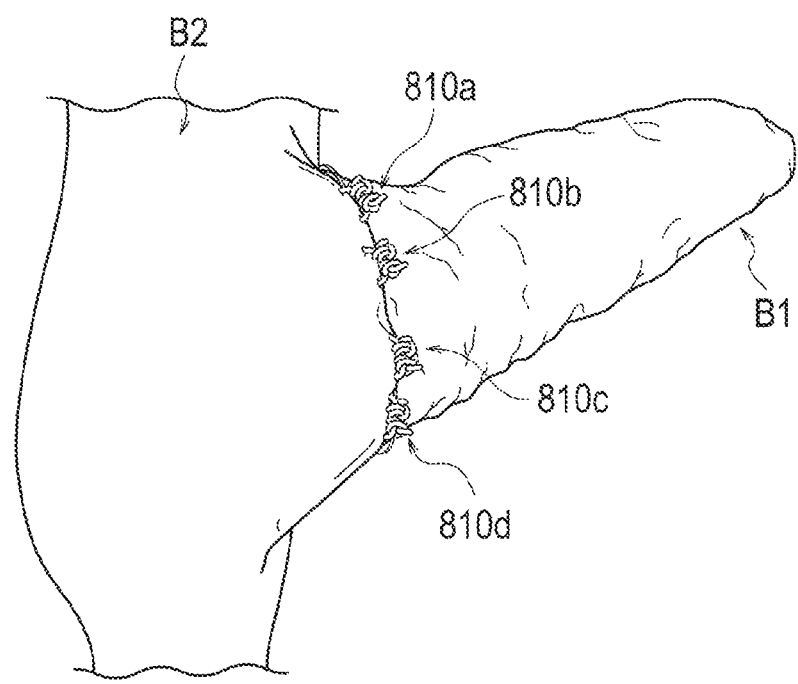
FIG. 24 is a schematic perspective view illustrating a state of the treatment method according to the second embodiment.

As illustrated in FIG. 24, the operator causes the medical device 110 to indwell in a state where the main body portion 120 of the medical device 110 is interposed between the cut surface B1*a* of the pancreatic parenchyma B1 and the intestinal wall of the jejunum B2. While being in contact with the cut surface B1*a* of the pancreatic parenchyma B1 and the intestinal wall of the jejunum B2, the main body portion 120 of the medical device 110 is caused to indwell between the cut surface B1*a* of the pancreatic parenchyma B1 and the intestinal wall of the jejunum B2. In this position, the main body portion 120 of the medical device 110 promotes the adhesion between the biological tissue of the pancreatic parenchyma B1 and the biological tissue of the intestinal wall of the jejunum B2.

As described above, the treatment method according to the present embodiment may be applied to a medical procedure for joining the pancreatic parenchyma B1 and the jejunum B2 to each other. In some embodiments, the treatment method joins the periphery of the cut surface B1*a* of the cut pancreatic parenchyma B1 and the intestinal wall (jejunal serous muscle layer) of the jejunum B2 together. According to the treatment method, the main body portion 120 of the medical device 110 interposed between the cut surface B1*a* of the pancreatic parenchyma B1 and the intestinal wall of the jejunum B2 promotes the adhesion between the biological tissue of the pancreatic parenchyma B1 and the biological tissue of the intestinal wall of the jejunum B2. Accordingly, the promoted adhesion provides a completely sealed joint, or continuous seal at a surface area, between the biological tissue of the pancreatic parenchyma B1 and the intestinal wall of the jejunum B2 reducing the risk factors that contribute to anastomotic leakage after the pancreatic parenchyma-jejunum anastomosis is performed.

The main body portion 120 of the medical device 110 used for the treatment method according to the present embodiment may include the hole portion 130 which aligns the pancreatic duct B1*b* extending inside the pancreatic parenchyma B1 and the through-hole B2*a* formed on the intestinal wall of the jejunum B2 with each other. Then, in the treatment method according to the present embodiment, in a state where the main body portion 120 of the medical device 110 is brought into contact with the periphery of the cut surface B1*a* on which the pancreatic parenchyma B1 is cut and the periphery of the through-hole B2*a* formed on the intestinal wall of the jejunum B2, the pancreatic parenchyma B1 and the jejunum B2 are moved relatively closer to each other. In this manner, the main body portion 120 of the medical device 110 is interposed between the pancreatic parenchyma B1 and the jejunum B2. According to the above-described treatment method, in the pancreatic parenchyma-jejunum anastomosis, the main body portion 120 of the medical device 110 placed between the pancreatic parenchyma B1 and the intestinal wall of the jejunum B2 can prevent communication from being interfered between the pancreatic duct B1*b* and the jejunum B2. In addition, when the medical device 110 is placed in the pancreatic parenchyma B1, the operator can use the hole portion 130 formed in the main body portion 120 as a guide to align the hole portion 130 with the pancreatic duct B1b of the pancreatic parenchyma B1. Therefore, the medical device 110 can be easily aligned with a desired position of the pancreatic parenchyma B1.

Next, referring to FIGS. 25 and 26, a treatment method according to the second embodiment using a first alternative embodiment of a medical device will be described.

Figure 25:
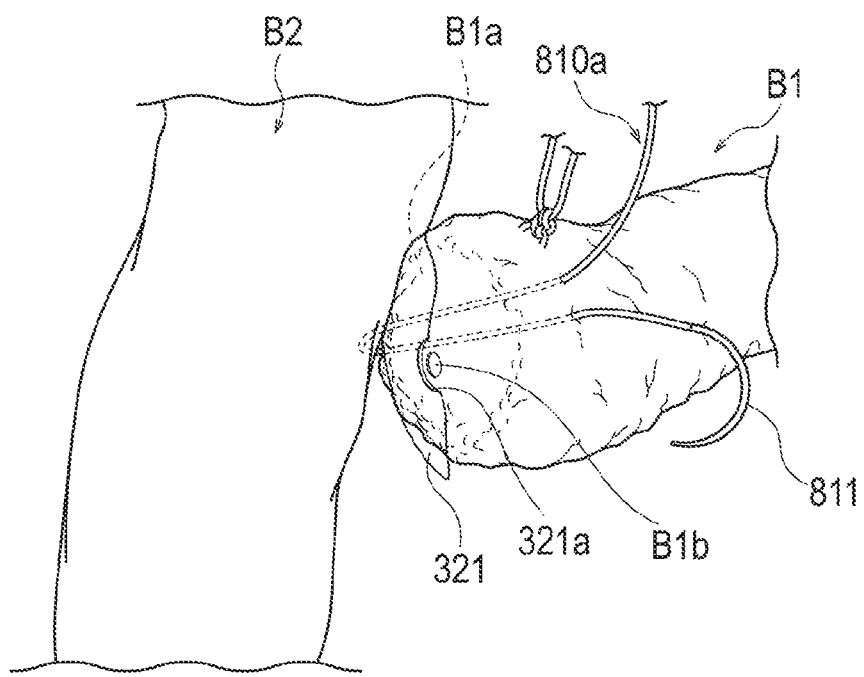
FIG. 25 is a schematic perspective view illustrating a state of the treatment method according to the second embodiment using a first alternative embodiment of a medical device.
Figure 26:
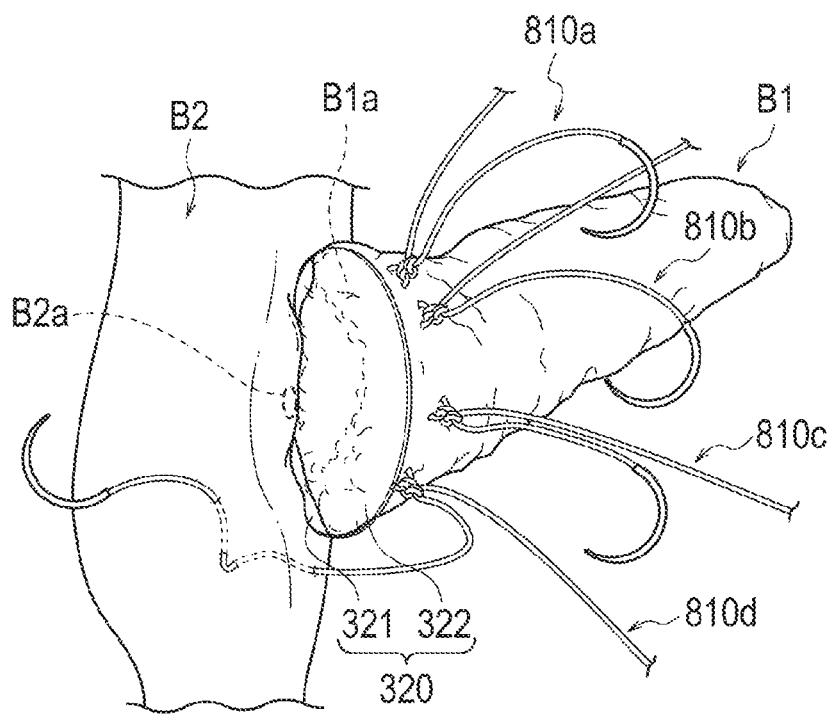
FIG. 26 is a schematic perspective view illustrating a state of the treatment method according to the second embodiment using the first alternative embodiment of the medical device.

As illustrated in FIGS. 25 and 26, the treatment method according to the second embodiment may employ the medical device 310 of FIG. 5 including the main body portion 320 having two split pieces 321 and 322.

As illustrated in FIG. 25, before the operator sutures the rear wall side of the pancreatic parenchyma B1 and the intestinal wall of the jejunum. B2, the operator attaches the first split piece 321 to the cut surface B1a of the pancreatic parenchyma B1. Next, the operator operates the double end needle 810a, thereby suturing the rear wall side of the pancreatic parenchyma B1, the intestinal wall of the jejunum B2, and the first split piece 321. Next, the operator performs a procedure the same as that according to the above-described treatment method (refer to FIG. 21), and uses the other double end needles 810b, 810c, and 810d. In a state where the first split piece 321 is interposed between the rear wall side of the pancreatic parenchyma B1 and the intestinal wall of the jejunum B2, the operator joins both of these to each other. In this case, the first split piece 321 may be sutured and fixed.

As illustrated in FIG. 26, the operator uses the respective double end needles 810a, 810b, 810c, and 810d to suture the rear wall side of the pancreatic parenchyma B1, the intestinal wall of the jejunum B2, and the first split piece 321. Thereafter, the operator attaches the second split piece 322 to a portion different from a portion having the first split piece 321 attached thereto on the cut surface B1a of the pancreatic parenchyma B1. The first split piece 321 and the second split piece 322 are placed adjacent to each another, thereby forming the hole portion 330 at a substantially center position of the main body portion 320 (refer to FIG. 5).

Next, the operator uses the double end needles 810a, 810b, 810c, and 810d. The operator joins the front wall side of the pancreatic parenchyma B1 and the intestinal wall of the jejunum B2 with the second split piece 322 interposed therebetween. In this case, the second split piece 322 may be sutured and fixed. While the operator brings the main body portion 320 of the medical device 310 into contact with the cut surface B1a of the pancreatic parenchyma B1 and the intestinal wall of the jejunum B2, the operator causes the main body portion 320 of the medical device 310 to indwell between the cut surface B1a of the pancreatic parenchyma B1 and the intestinal wall of the jejunum B2.

According to the treatment method in the present modification example, the first split piece 321 configuring the main body portion 320 of the medical device 310 is attached to the cut surface B1a of the pancreatic parenchyma B1 before the rear wall side of the pancreatic parenchyma B1 and the intestinal wall of the jejunum B2 are sutured. The operator attaches the second split piece 322 configuring the main body portion 320 of the medical device 310 to the cut surface B1a of the pancreatic parenchyma B1 before the front wall side of the pancreatic parenchyma B1 and the intestinal wall of jejunum B2 are sutured. Therefore, the work for attaching the first split piece 321 to the cut surface B1a of the pancreatic parenchyma B1 can be easily carried out, and the work for attaching the second split piece 322 to the cut surface B1a of the pancreatic parenchyma B1 can be easily carried out.

Next, referring to FIGS. 27 and 28, a treatment method according to the second embodiment using a second alternative embodiment of a medical device will be described.

Figure 27:
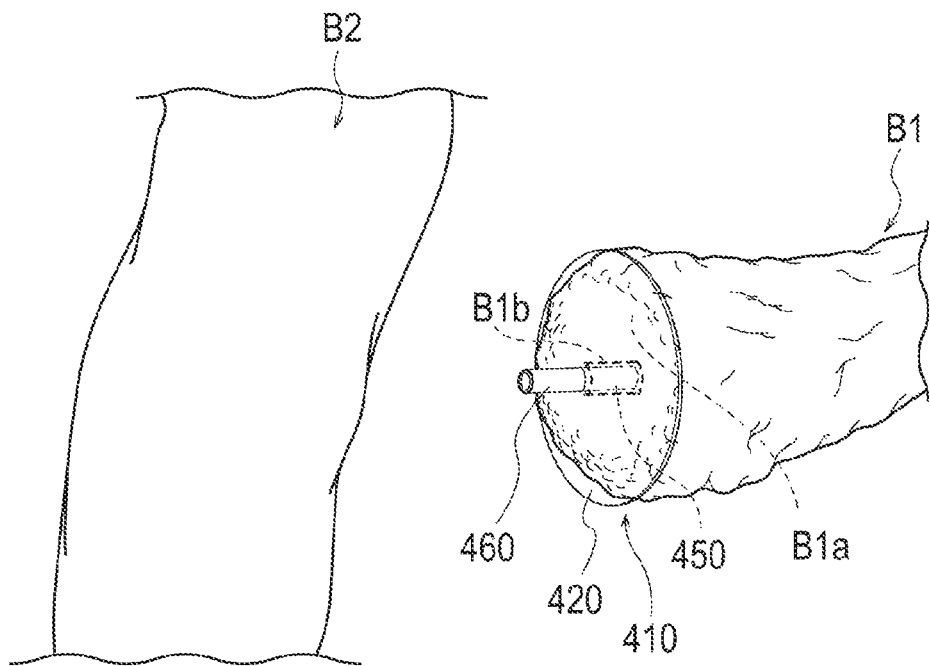
FIG. 27 is a schematic perspective view illustrating a state of the treatment method according to the second embodiment using a second alternative embodiment of a medical device.
Figure 28:
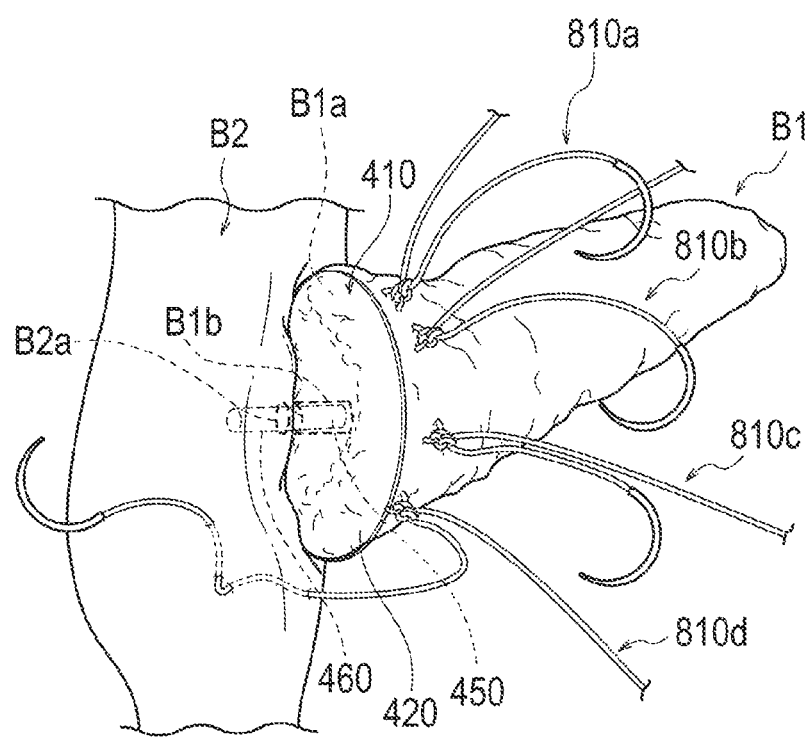
FIG. 28 is a schematic perspective view illustrating a state of the treatment method according to the second embodiment using the second alternative embodiment of the medical device.

As illustrated in FIGS. 27 and 28, the treatment method according to the second embodiment may employ the medical device 410 of FIG. 6 including the first tubular portion 450 and the second tubular portion 460.

As illustrated in FIG. 27, the operator inserts the first tubular portion 450 of the medical device 410 into the pancreatic duct B1b before suturing the pancreatic parenchyma B1 and the jejunum B2. The main body portion 420 of the medical device 410 is attached to the cut surface B1a of the pancreatic parenchyma B1. The operator can easily place the medical device 410 in the pancreatic parenchyma B1 by inserting the first tubular portion 450 into the pancreatic duct B1b.

As illustrated in FIG. 28, the operator inserts the second tubular portion 460 of the medical device 410 into the through-hole B2a formed in the jejunum B2. The medical device 410 allows the pancreatic duct B1b and an interior of the jejunum B2 to communicate with each other via the first tubular portion 450 and the second tubular portion 460. The main body portion 420 of the medical device 410 is interposed between the cut surface B1a of the pancreatic parenchyma B1 and the jejunum B2. The timing at which the through-hole B2a is formed in the jejunum B2 is not particularly limited as long as the timing is before the second tubular portion 460 is inserted into the through-hole B2a.

As described above, the treatment method according to the present modification example employs the medical device 410 including the first tubular portion 450 and the second tubular portion 460. In this manner, the pancreatic duct B1b and the interior of the jejunum B2 are allowed to communicate with each other.

In addition, as described above, the through-holes 25 are formed in the main body portion 420 and the first tubular portion 450 which are included in the medical device 410 (refer to FIG. 6). Therefore, the medical device 410 can favorably promote the adhesion among the pancreatic parenchyma B1, the pancreatic duct B1b, and the jejunum B2 by using the main body portion 420 and the first tubular portion 450. Through-holes 25 may also be formed in the outer member 461 of the second tubular portion 460 included in the medical device 410. Therefore, the outer member 461 of the second tubular portion 460 can be placed in contact with the inner surface of the jejunum B2, thereby promoting adhesion to the jejunum B2. On the other hand, the through-holes 25 may not be formed in the inner member 462 of the second tubular portion 460. Therefore, the second tubular portion 460 can prevent crushing and kinking. Therefore, the second tubular portion 460 can maintain a flow path formed by a lumen of the inner member 462 in a proper shape, and it is possible to prevent stenosis caused by the narrowed lumen of the inner member 462. Furthermore, the through-holes 25 may not be formed in the inner member 462 of the second tubular portion 460. Accordingly, it is possible to prevent the stenosis in the lumen of the inner member 462, which is caused by biological components (for example, protein) accumulating in the through-holes 25.

In the treatment method according to the second embodiment, for example, the medical device 210 illustrated in FIG. 4 can be used. In a case of using the medical device 210 of FIG. 4, the operator causes the pancreatic duct tube 830 to pass through the slit 240 formed in the main body portion 220 in a state where the pancreatic duct tube 830 is inserted into the pancreatic duct B1b and the through-hole B2a of the jejunum B2. In this manner, the main body portion 220 can be placed between the cut surface B1a of the pancreatic parenchyma B1 and the intestinal wall of the jejunum B2.

Figure 29:
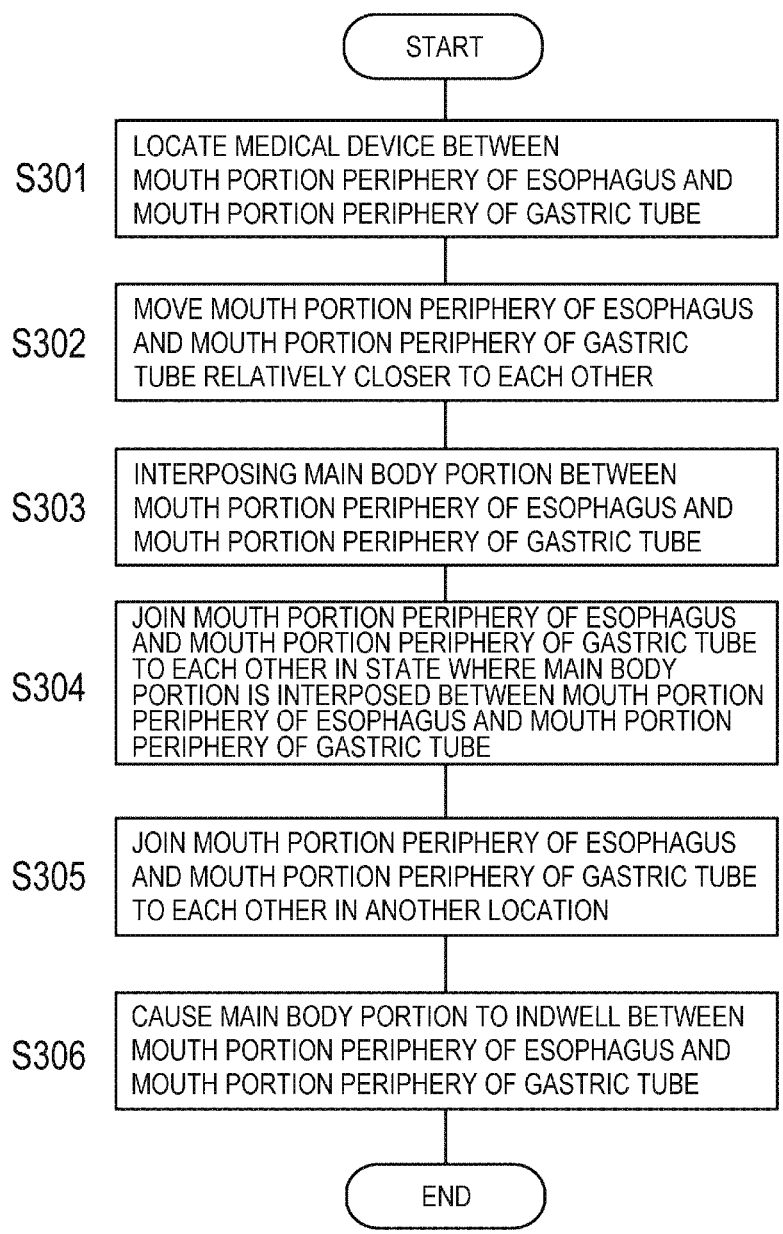
FIG. 29 is a flowchart illustrating a treatment method in accordance with a third embodiment of the present disclosure.

FIG. 29 is a flowchart illustrating a procedure of esophagus-gastric tube anastomosis according to a third embodiment, and FIGS. 30 to 41 are views illustrating various states, or stages, of the esophagus-gastric tube anastomosis according to the third embodiment.

In the treatment method according to the present embodiment, biological organs to be joined may include an esophagus cut due to excision of a cancer tumor or other object, and a reconstructive gastric tube (hereinafter, referred to as a gastric tube) which is a biological organ other than the esophagus. In the following description, a procedure will be described in which a mouth portion periphery (a first joint target site) of a cut esophagus C1 and a mouth portion periphery (a second joint target sites) of a gastric tube C2 are joined to each other. In the present embodiment, an example using the medical device 510 of FIG. 7 will be described.

As illustrated in FIG. 29, anastomosis according to the present embodiment may include placing the medical device between the mouth portion periphery of the esophagus and the mouth portion periphery of the gastric tube (S301), moving the mouth portion periphery of the esophagus and the mouth portion periphery of the gastric tube relatively closer to each other (S302), interposing the main body portion of the medical device between the mouth portion periphery of the esophagus and the mouth portion periphery of the gastric tube (S303), joining both of these in a state where the main body portion of the medical device is interposed between the mouth portion periphery of the esophagus and the mouth portion periphery of the gastric tube (S304), joining both of these in a state where the main body portion of the medical device in another location between the mouth portion periphery of the esophagus and the mouth portion periphery of the gastric tube (S305), and causing the main body portion of the medical device to indwell between the mouth portion periphery of the esophagus and the mouth portion periphery of the gastric tube (S306).

Next, referring to FIGS. 30 to 41, the treatment method according to the present embodiment will be described in detail. In the present embodiment, a triangular anastomosis of esophagus-gastric tube will be described.

Figure 30:
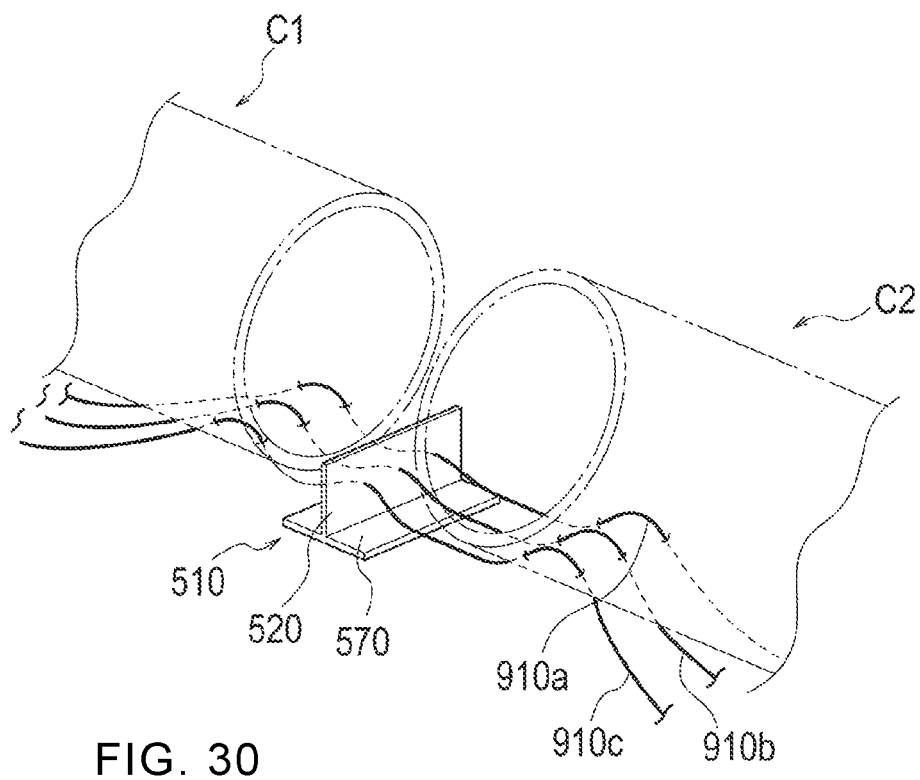
FIG. 30 is a schematic perspective view illustrating a state of the treatment method according to the third embodiment of the present disclosure.

As illustrated in FIG. 30, the operator hangs support sutures 910a, 910b, and 910c on an esophagus C1 and a gastric tube C2. When the operator hangs the respective support sutures 910a, 910b, and 910c on the esophagus C1 and the gastric tube C2, the operator places the medical device 510 between the esophagus C1 and the gastric tube C2 by causing the respective support sutures 910a, 910b, and 910c to pass through the main body portion 520 of the medical device 510. For example, the respective support sutures 910a, 910b, and 910c can be configured to include a known suture provided with bioabsorbability.

Figure 31:
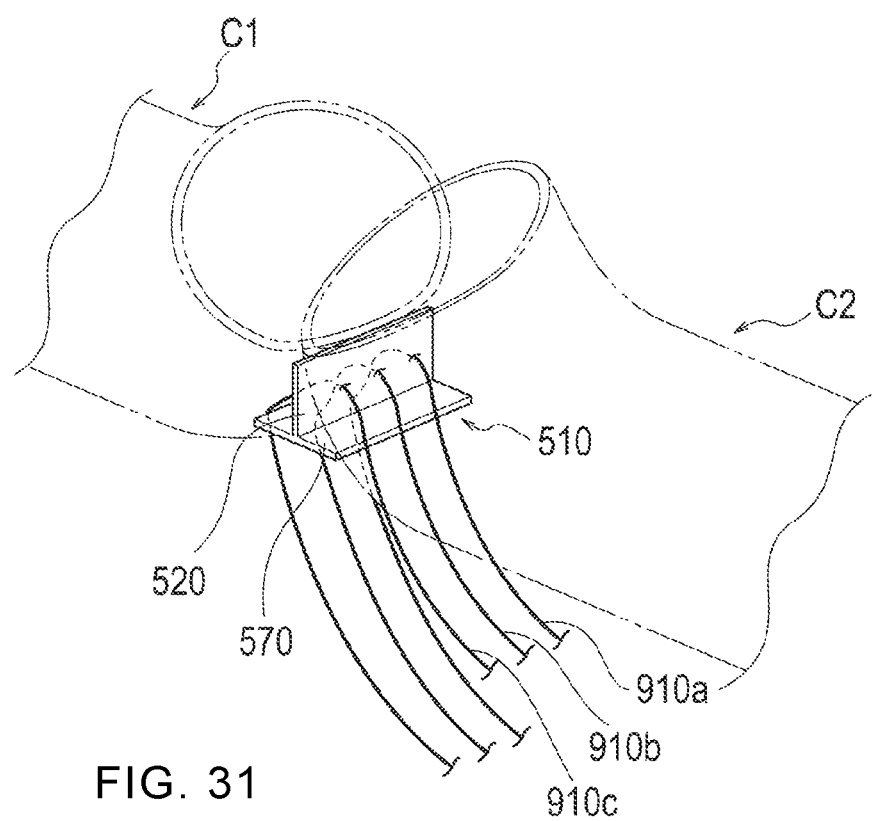
FIG. 31 is a schematic perspective view illustrating a state of the treatment method in accordance with the third embodiment.

Next, as illustrated in FIG. 31, the operator operates the respective support sutures 910a, 910b, and 910c, and moves the esophagus C1 and the gastric tube C2 relatively closer to each other while lifting both of these. The operator interposes the main body portion 520 of the medical device 510 between the esophagus C1 and the gastric tube C2 by moving the esophagus C1 and the gastric tube C2 relatively closer to each other.

Figure 32:
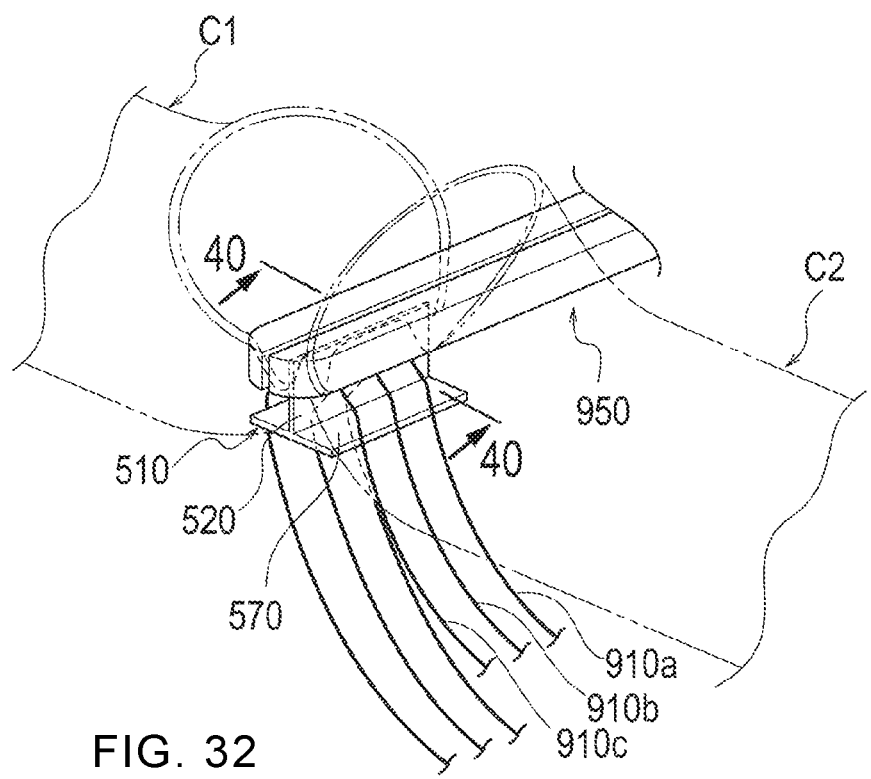
FIG. 32 is a schematic perspective view illustrating a state of the treatment method according to the third embodiment.
Figure 40:
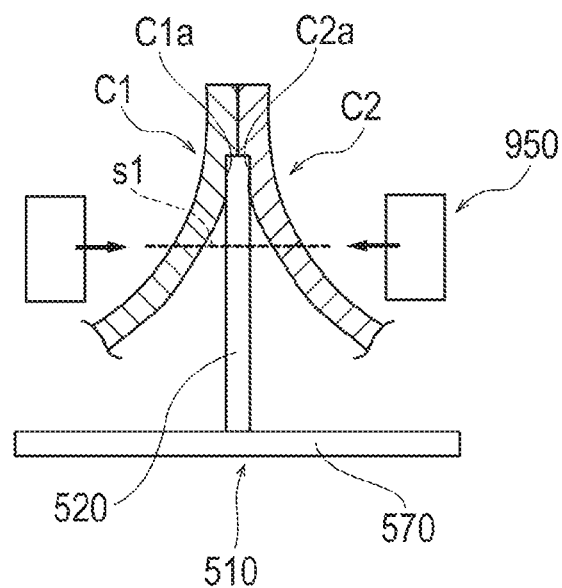
FIG. 40 is a view briefly illustrating a portion of a cross section taken along line 40-40 illustrated in FIG. 32.

Here, FIG. 40 illustrates a sectional view (schematic sectional view of a portion illustrated by arrow 40-40 in FIG. 32) in a state where the main body portion 520 of the medical device 510 is interposed between the esophagus C1 and the gastric tube C2. As illustrated in FIG. 40, for example, the operator can place a portion of the main body portion 520 of the medical device 510 between an outer surface C1a of the esophagus C1 and an outer surface C2a of the gastric tube C2. In a state where the main body portion 520 of the medical device 510 is placed in this way, the operator performs suturing by using an automatic suturing device 950 (to be described later). A suturing location sutured using the automatic suture device 950 can be set to a portion where the outer surface C1a of the esophagus C1, the main body portion 520 of the medical device 510, and the outer surface C2a of the gastric tube C2 overlap one on another (for example, a portion indicated by a broken line s1 in FIG. 40). In addition, when suturing work is carried out for the esophagus C1 and the gastric tube C2 by using the automatic suture device 950, based on a position of the guide portion 570, it is possible to control (determine) an excision position (position in the upward-downward direction in FIG. 40) of the main body portion 520 of the medical device 510. In this manner, the operator can smoothly carry out the suturing work by using the automatic suture device 950.

Next, as illustrated in FIG. 32, the operator sutures the esophagus C1, the gastric tube C2, and the main body portion 520 of the medical device 510 by using the automatic suture device 950. The suturing work using the automatic suture device 950 can be carried out by staples 951 (refer to FIG. 33) loaded in the automatic suture device 950. When the suturing work is carried out using the automatic suture device 950, the operator excises the esophagus C1, the gastric tube C2, and a portion of the main body portion 520 of the medical device 510 by using the automatic suture device 950. For example, similar to the automatic suture device 950, a known device may be used for the esophagus-gastric tube anastomosis.

Figure 33:
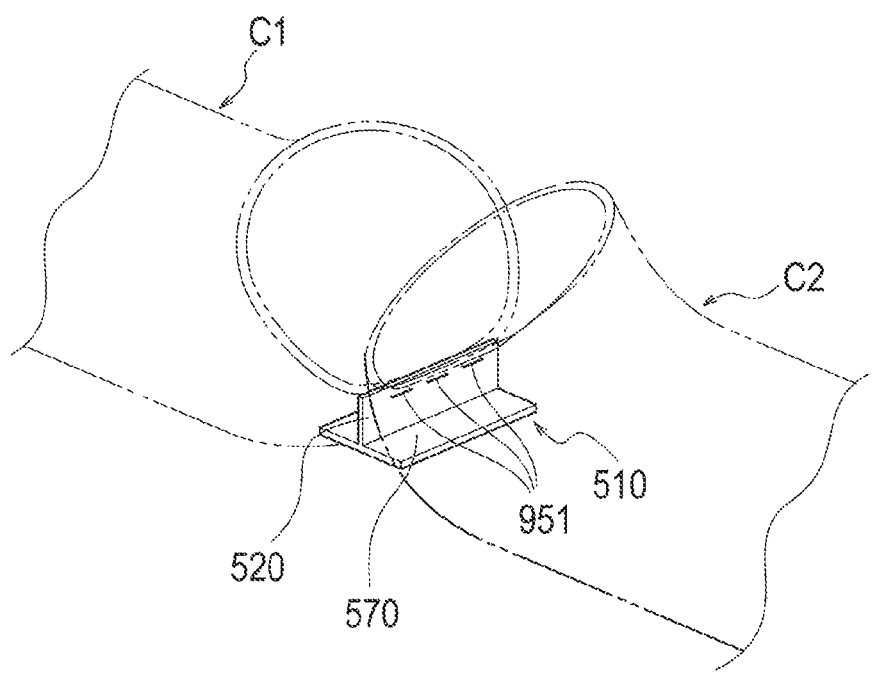
FIG. 33 is a schematic perspective view illustrating a state of the treatment method according to the third embodiment.

FIG. 33 illustrates the esophagus C1, the gastric tube C2, and the medical device 510 in a state where the suturing work is completely carried out using the automatic suture device 950. After the suturing work is completely carried out, the operator causes the medical device 510 to indwell in a state where a portion of the main body portion 520 is interposed between the esophagus C1 and the gastric tube C2.

Next, the operator carries out the suturing work for another location (another location in the circumferential direction in the esophagus C1 and the gastric tube C2) where the suturing work is not carried out in the esophagus C1 and the gastric tube C2.

Figure 34:
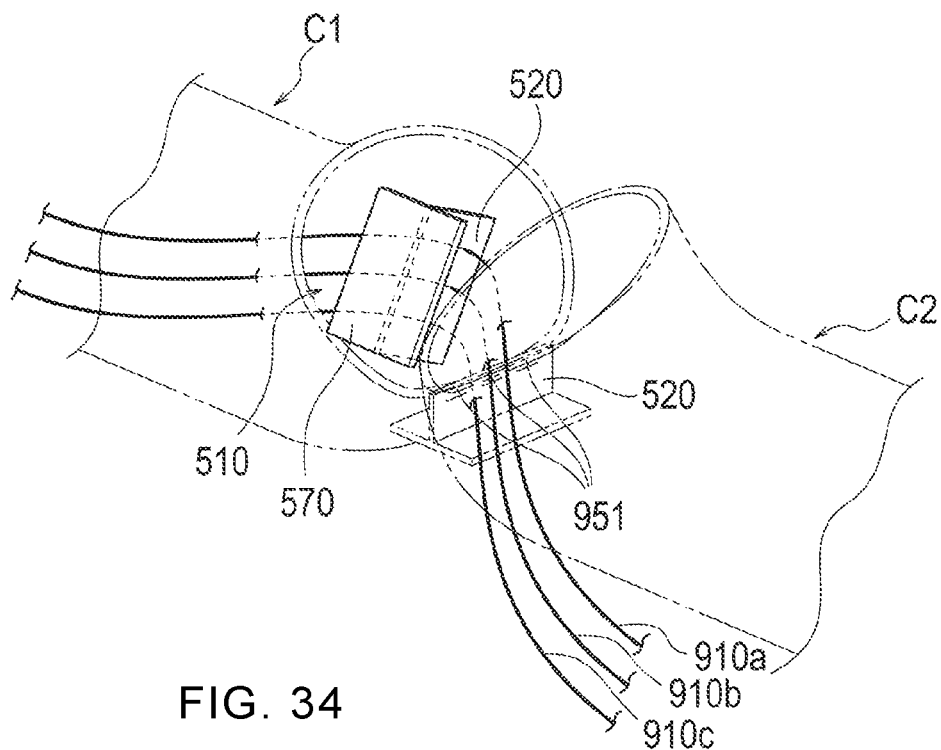
FIG. 34 is a schematic perspective view illustrating a state of the treatment method according to the third embodiment.
Figure 35:
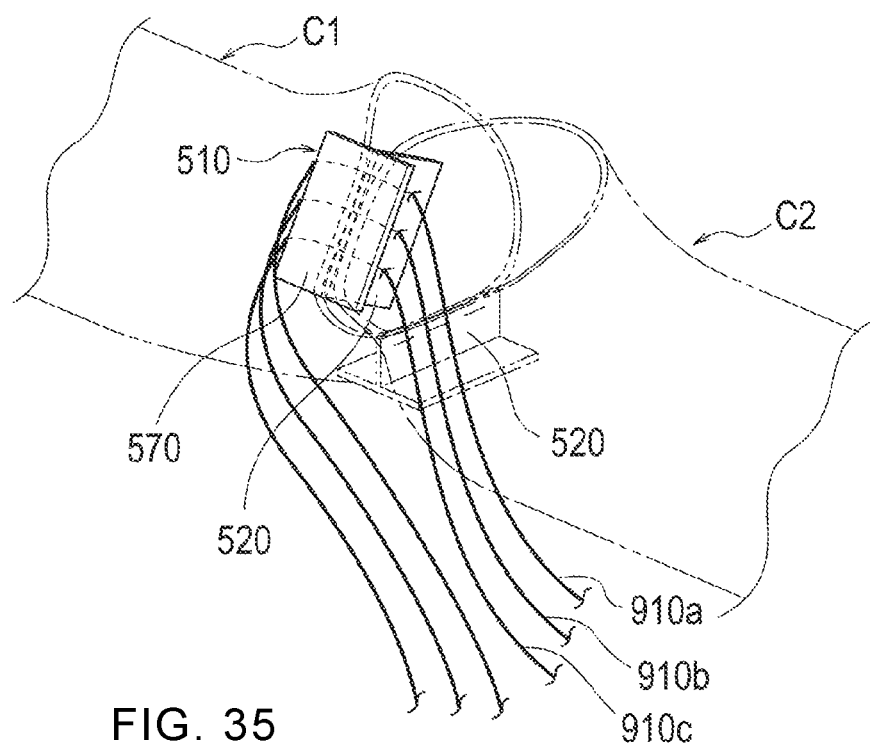
FIG. 35 is a schematic perspective view illustrating a state of the treatment method according to the third embodiment.

As illustrated in FIG. 34, the operator hangs the support sutures 910a, 910b, and 910c on the esophagus C1 and the gastric tube C2. When the operator hangs the respective support sutures 910a, 910b, and 910c on the esophagus C1 and the gastric tube C2, the operator places the medical device 510 between the esophagus C1 and the gastric tube C2 by causing the respective support sutures 910a, 910b, and 910c to pass through the main body portion 520 of the medical device 510. In addition, as illustrated in FIG. 35, the operator operates the respective support sutures 910a, 910b, and 910c, and moves the esophagus C1 and the gastric tube C2 relatively closer to each other while lifting both of these. The operator interposes the main body portion 520 of the medical device 510 between the esophagus C1 and the gastric tube C2 by moving the esophagus C1 and the gastric tube C2 relatively closer to each other.

Figure 41:
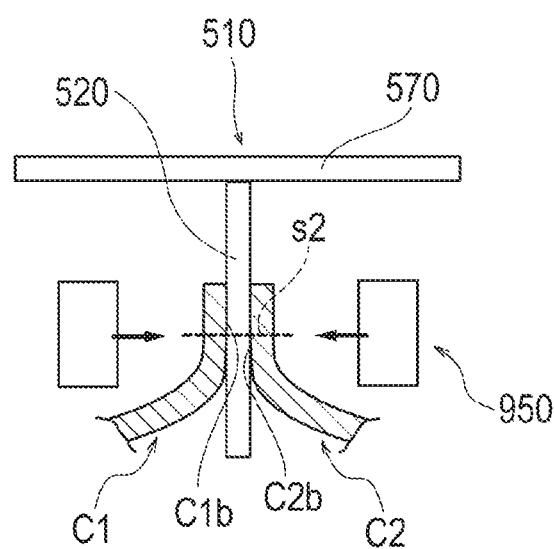
FIG. 41 is a view briefly illustrating a portion of a cross section taken along line 41-41 illustrated in FIG. 36.

Here, FIG. 41 illustrates a sectional view (schematic sectional view of a portion illustrated by arrow 41-41 in FIG.

36) in a state where the main body portion 520 of the medical device 510 is interposed between the esophagus C1 and the gastric tube C2. As illustrated in FIG. 41, the operator can place a portion of the main body portion 520 of the medical device 510 between the inner surface C1b of the esophagus C1 and the inner surface C2b of the gastric tube C2. The operator carries out the suturing work by using the automatic suture device 950 in a state where the main body portion 520 of the medical device 510 is placed in this way. A suturing location sutured using the automatic suture device 950 can be set to a portion where the outer surface C1b of the esophagus C1, the main body portion 520 of the medical device 510, and the outer surface C2b of the gastric tube C2 overlap one on another (for example, a portion indicated by a broken line s2 in FIG. 41). In addition, when the suturing work is carried out for the esophagus C1 and the gastric tube C2 by using the automatic suture device 950, based on a position of the guide portion 570, it is possible to determine an excision position (position in the upward-downward direction in FIG. 41) of the main body portion 520 of the medical device 510. In this manner, the operator can smoothly carry out excision-suturing work by using the automatic suture device 950.

Figure 36:
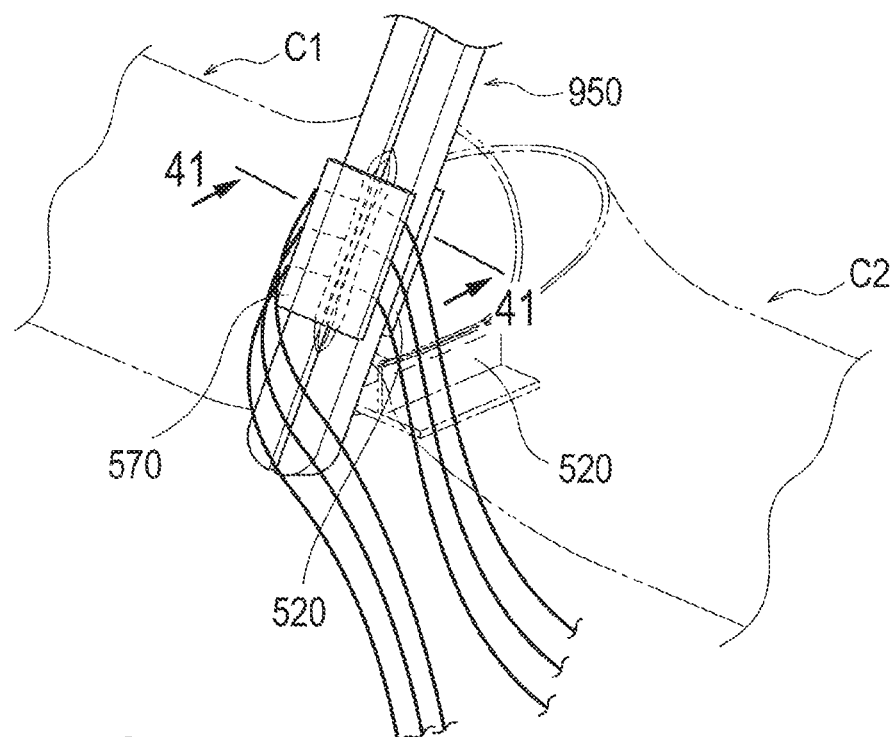
FIG. 36 is a schematic perspective view illustrating a state of the treatment method according to the third embodiment.

Next, as illustrated in FIG. 36, the operator sutures the esophagus C1, the gastric tube C2, and the main body portion 520 of the medical device 510 by using the automatic suture device 950. In addition, when the suturing work is carried out using the automatic suture device 950, the operator excises the esophagus C1, the gastric tube C2, and a portion of the main body portion 520 of the medical device 510 by using the automatic suture device 950.

Figure 37:
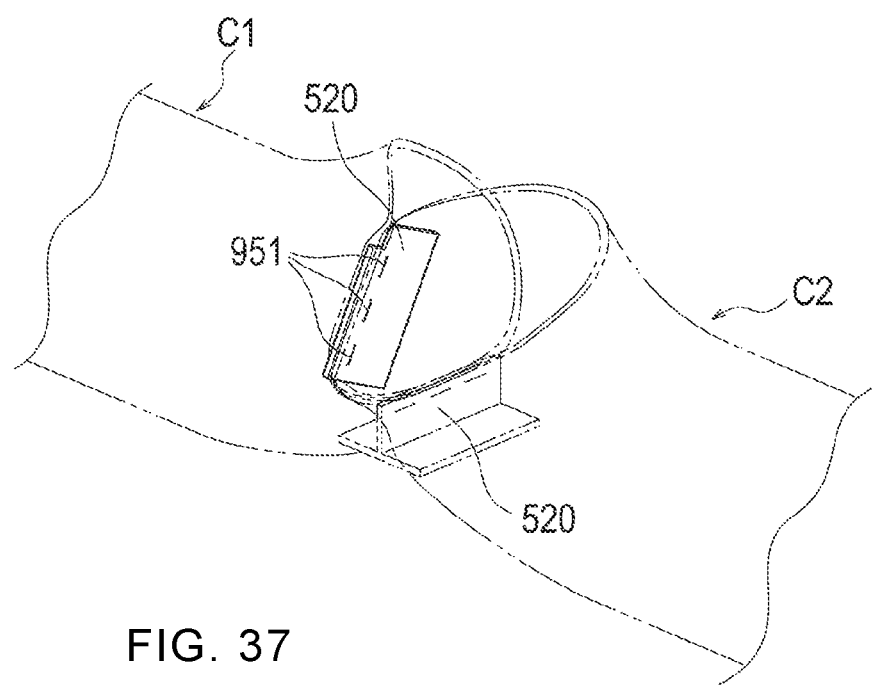
FIG. 37 is a schematic perspective view illustrating a state of the treatment method according to the third embodiment.

FIG. 37 illustrates the esophagus C1, the gastric tube C2, and the medical device 510 in a state where the suturing work is completely carried out using the automatic suture device 950. After the suturing work is completely carried out, the operator causes the medical device 510 to indwell in a state where a portion of the main body portion 520 is interposed between the mouth portion periphery of the esophagus C1 and the mouth portion periphery of the gastric tube C2. The operator carries out the above-described work. In this manner, the operator can suture the esophagus C1 and the gastric tube C2 in another location different from the suturing location illustrated in FIGS. 30 to 33. In a stage where the work is completely carried out so far, the esophagus C1 and the gastric tube C2 are in a joined state at two different locations in the circumferential direction of the esophagus C1 and the gastric tube C2.

Figure 38:
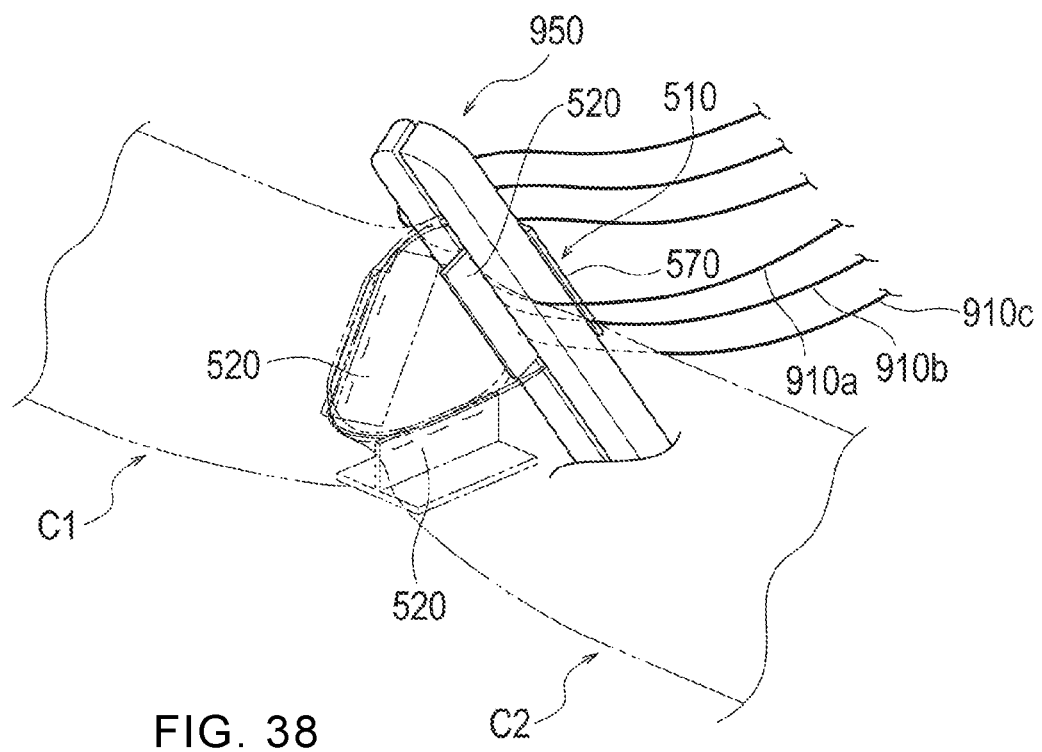
FIG. 38 is a schematic perspective view illustrating a state of the treatment method according to the third embodiment.

Next, the operator carries out the suturing work for still another location where the suturing work is not carried out in the esophagus C1 and the gastric tube C2. Specifically, as illustrated in FIG. 38, the operator sutures a portion which is not joined in the esophagus C1 and the gastric tube C2. A specific procedure of the suturing work is substantially the same as the procedure illustrated in FIGS. 34 to 37 except for the suturing location. Accordingly, the description thereof will be omitted for the sake of clarity and conciseness.

Figure 39:
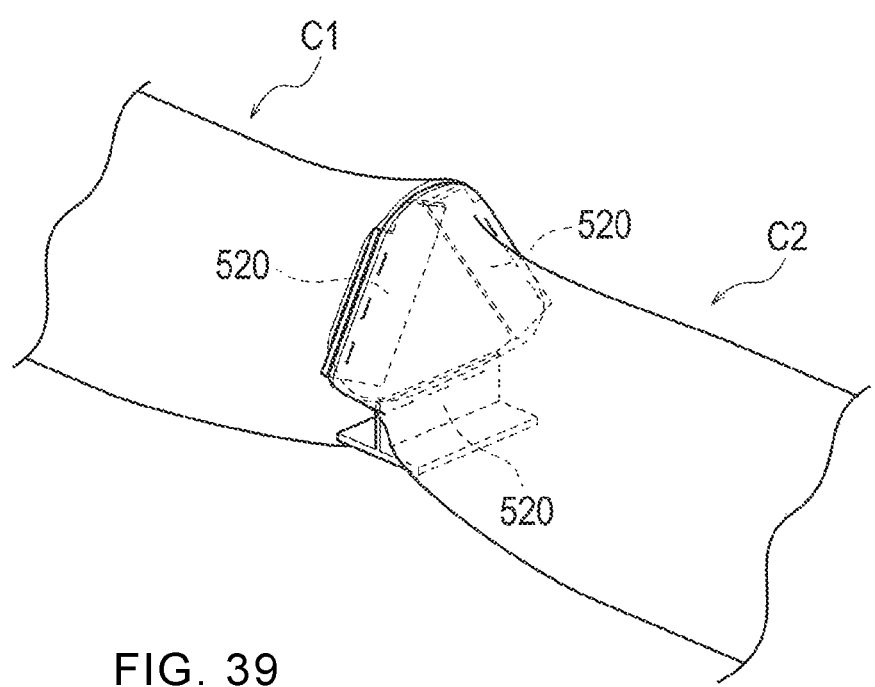
FIG. 39 is a schematic perspective view illustrating a state of the treatment method according to the third embodiment.

FIG. 39 illustrates the esophagus C1, the gastric tube C2, the medical device 510 in a state where the suturing work is completely carried out using the automatic suture device 950. The operator sutures the esophagus C1 and the gastric tube C2 at three different locations in the circumferential direction by carrying out work described above. In addition, the operator causes the medical device 510 to indwell in a state where the main body portion 520 of the medical device 510 is interposed between the esophagus C1 and the gastric tube C2 in each portion of the above-described three locations.

After the suturing work is completely carried out for the esophagus C1 and the gastric tube C2, the operator can appropriately excise an unnecessary portion of each medical device 510 (portion protruding from between the esophagus C1 and the gastric tube C2).

As described above, the treatment method according to the present embodiment is used for the medical procedure for joining the esophagus and the gastric tube to each other. In addition, according to the above-described treatment method, the mouth portion periphery of the esophagus C1 and the mouth portion periphery of the gastric tube C2 are joined to each other. According to the treatment method, the main body portion 520 of the medical device 510 placed between the mouth portion periphery of the esophagus C1 and the mouth portion periphery of the gastric tube C2 can promote the adhesion between the biological tissue of the mouth portion periphery of the esophagus C1 and the biological tissue of the mouth portion periphery of the gastric tube C2. Accordingly, this promoted adhesion between tissues provides a complete and continuous peripheral seal at the excised area that, among other things, serves to reduce the risk factors that contribute to anastomotic leakage after the esophagus-gastric tube anastomosis is performed.

In addition, according to the present embodiment, in a state where the main body portion 520 of the medical device 510 is placed between the mouth portion periphery of the esophagus C1 and the mouth portion periphery of the gastric tube C2, the mouth portion periphery of the esophagus C1 and the mouth portion periphery of the gastric tube C2 are moved relatively closer to each other. In this manner, the main body portion 520 of the medical device 510 is interposed between the mouth portion periphery of the esophagus C1 and the mouth portion periphery of the gastric tube C2. Therefore, the operator carries out easy work for moving the mouth portion periphery of the esophagus C1 and the mouth portion periphery of the gastric tube C2 relatively closer to each other. In this manner, the operator can interpose the main body portion 520 of the medical device 510 between the mouth portion periphery of the esophagus C1 and the mouth portion periphery of the gastric tube C2.

In addition, according to the present embodiment, in a state where the main body portion 520 of the medical device 510 is interposed between the mouth portion periphery of the esophagus C1 and the mouth portion periphery of the gastric tube C2, the mouth portion periphery of the esophagus C1 and the mouth portion periphery of the gastric tube C2 are joined to each other at a plurality of locations different in the circumferential direction of the esophagus C1 and the gastric tube C2. Therefore, in the medical procedure using the medical device 510, the operator can perform the triangular anastomosis of esophagus-gastric tube, for example.

In addition, according to the present embodiment, the medical device 510 may comprise the guide portion 570 for guiding the joint position of the main body portion 520 of the medical device 510 to the mouth portion periphery of the esophagus C1 and the mouth portion periphery of the gastric tube C2. Then, when the operator joins the mouth portion periphery of the esophagus C1 and the mouth portion periphery of the gastric tube C2 to each other, the operator controls the joint position of the main body portion 520 of the medical device 510 by using the guide portion 570.

Therefore, the operator can easily align the joint position of the main body portion 520 of the medical device 510.

Next, referring to FIG. 42, a treatment method according to the third embodiment using a modified embodiment of a medical device will be described.

Figure 42:
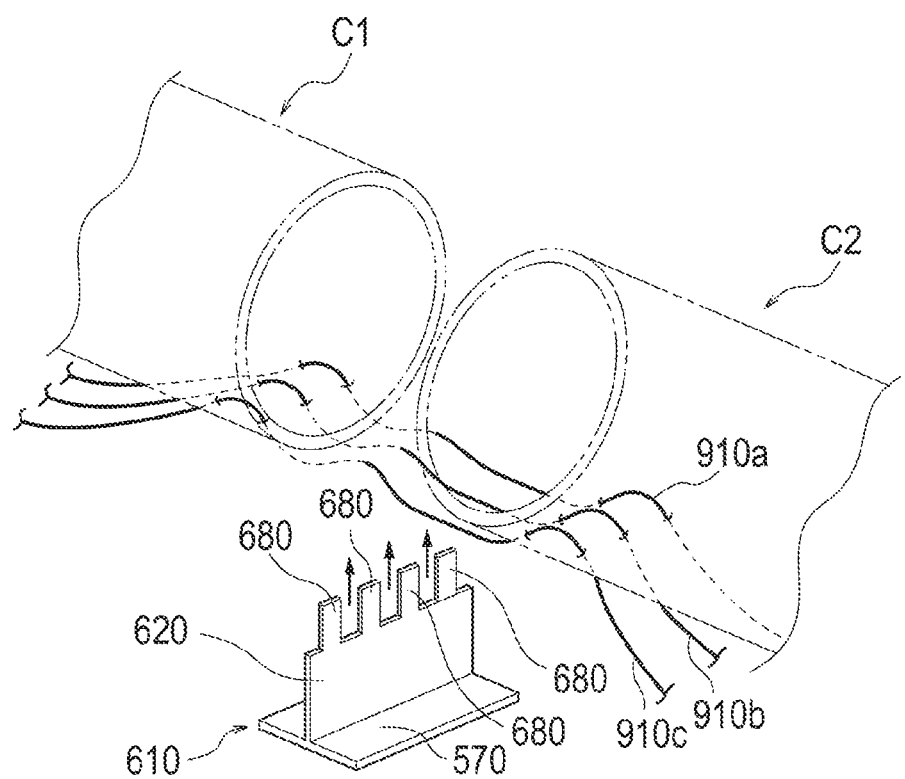
FIG. 42 is a schematic perspective view illustrating a state of the treatment method according to the third embodiment using a modified embodiment of a medical device.

As illustrated in FIG. 42, in the treatment method according to the modification example, the medical device 610 of FIG. 8 including the main body portion 620, the guide portion 570, and the protruding portion 680 may be used.

As illustrated in FIG. 42, in a state where the operator hangs the support sutures 910*a*, 910*b*, and 910*c* on the mouth portion periphery of the esophagus C1 and the mouth portion periphery of the gastric tube C2, the operator places the medical device 610 between the mouth portion periphery of the esophagus C1 and the mouth portion periphery of the gastric tube C2. In this case, the operator causes the respective support sutures 910*a*, 910*b*, and 910*c* to pass through a gap formed between the protruding portions 680 adjacent to each other. In this manner, the operator can easily place the main body portion 620 of the medical device 610 between the mouth portion periphery of the esophagus C1 and the mouth portion periphery of the gastric tube C2. Other procedures associated with this treatment method are substantially similar to, or the same as, those previously described in conjunction with the third embodiment, and thus, description thereof will be omitted for the sake of clarity and conciseness. In a case of performing the triangular anastomosis of the esophagus-gastric tube described in the third embodiment and the modification example, it is possible to place different types of the medical devices for each joining location, for example.

As described in the above-described respective embodiments, the treatment method according to the present disclosure may include placing the medical device including the sheet-like main body portion for promoting the adhesion of the biological tissues between one joint target site and the other joint target site of the biological organ to be joined, and joining the one joint target site and the other joint target site in a state where at least a portion of the main body portion is interposed between the one joint target site and the other joint target site. According to the present treatment method, it is possible to reduce the risk factors contributing to anastomotic leakage after the medical joining procedure (for example, anastomosis of a digestive tract) by using an easy method of interposing the sheet-like main body portion included in the medical device between the one joint target site and the other joint target site, which, among other things, creates a completely sealed surface area between portions of the digestive tract.

In addition, according to the above-described treatment method, when the medical device is placed, at least a portion of the main body portion of the medical device is brought into contact with the outer surface of the one joint target sites and/or the outer surface of the other joint target site. Therefore, the medical device can temporarily stay in the vicinity of the joint target site by attaching the main body portion of the medical device to the outer surface of the joint target site. Accordingly, the medical procedure can be smoothly executed.

In addition, the above-described treatment method may include interposing the main body portion between the one joint target site and the other joint target site by moving the one joint target site and the other joint target site relatively closer to each other, in a state where the main body portion of the medical device is placed between the one joint target site and the other joint target site. Therefore, the main body portion of the medical device can be interposed between the joint target sites by carrying out easy work for moving the joint target sites relatively closer to each other.

In addition, the above-described treatment method may include joining at least a portion of the main body portion to the first joint target site and/or the second joint target site while joining the first joint target site and the second joint target site to each other. Therefore, the main body portion of the medical device can be more reliably fixed to the respective joint target sites. Accordingly, the adhesion between the joint target sites can be promoted by the medical device after the main body portion of the medical device is caused to indwell.

In addition, according to the above-described treatment method, the joining may be performed using the stapler and/or the suture. Therefore, the operator can easily join the joint target sites to each other by using the stapler or the suture.

Next, a treatment method (pancreatic parenchyma-jejunum anastomosis) according to the above-described second embodiment and where a third alternative embodiment of a medical device (e.g., the medical device 1010 of FIG. 44) can be used, will be described. In the following example, contents the same as those previously described in the above-described second embodiment and the use of alternative embodiments of the medical devices associated therewith will be omitted for the sake of clarity and conciseness.

Figure 43:
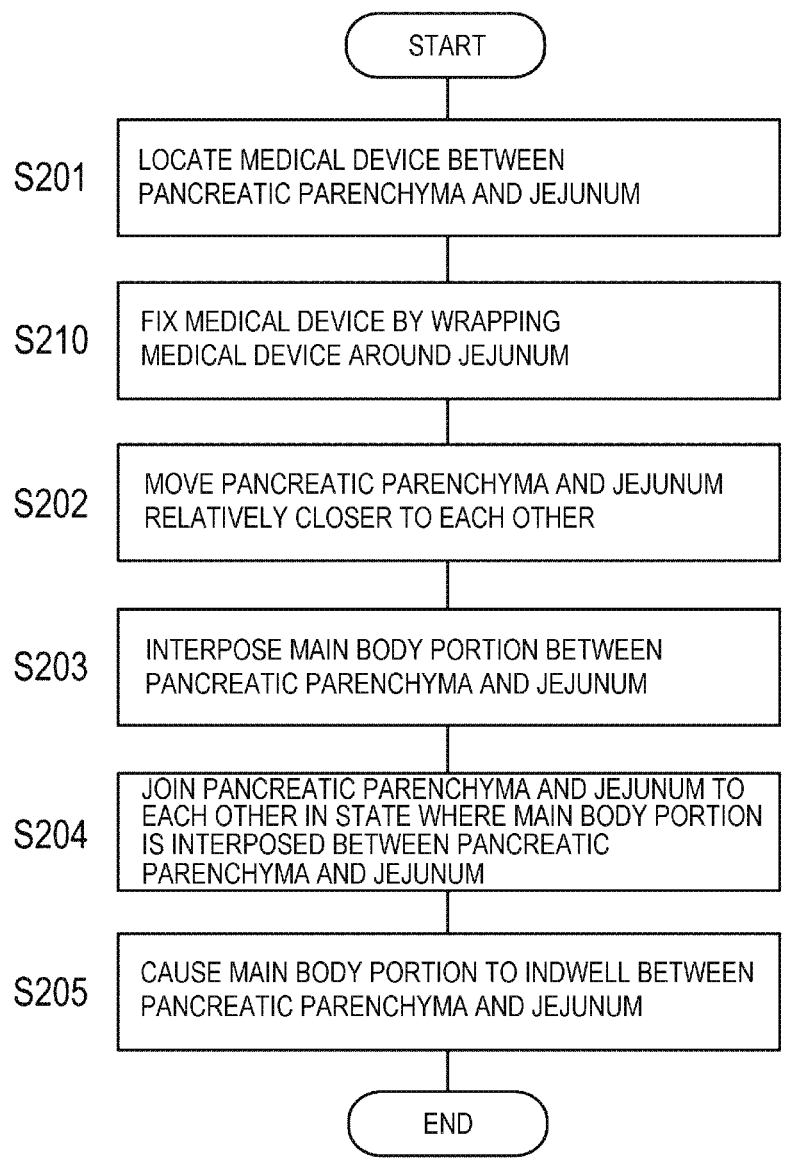
FIG. 43 is a flowchart illustrating a treatment method according to the second embodiment using a third alternative embodiment of a medical device.

FIG. 43 is a flowchart illustrating each procedure of the treatment method according to the second embodiment using a third alternative embodiment of a medical device. As illustrated in FIG. 43, the treatment method may be different from the treatment method according to the above-described second embodiment in that the treatment method may include fixing the medical device by wrapping the medical device around the jejunum (S210) (refer to FIG. 14). The above-described work (S210) can be carried out simultaneously with the work (S201) of placing the medical device between the pancreatic parenchyma and the jejunum, or after the work (S201) is completely carried out.

The medical device 1010 shown in FIG. 44 will now be described.

Figure 44:
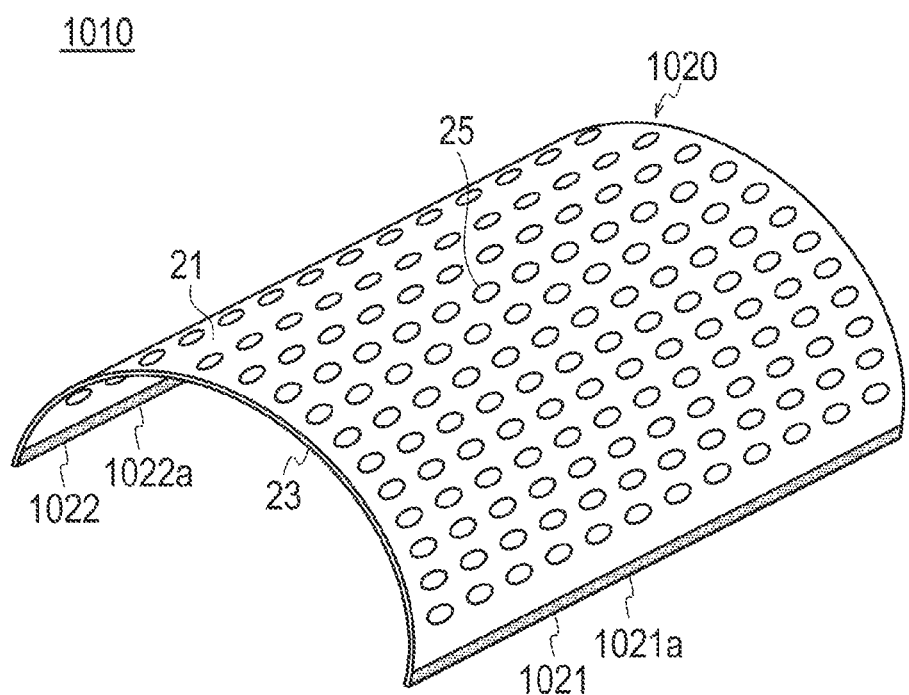
FIG. 44 is a perspective view of the third alternative embodiment of the medical device used in the treatment method according to FIG. 43.

As illustrated in FIG. 44, the medical device 1010 may comprise a sheet-like main body portion 1020 having through-holes 25 formed therein. The through-holes 25 penetrate along the thickness direction of the main body portion 20.

As illustrated in FIG. 44, in a natural state where no external force is applied, the main body portion 1020 may have an arc shape in which one surface side (front surface 21 side in the illustrated example) is curved in a convex shape. In the main body portion 1020, the arc shape may be formed in advance. As will be described later, the main body portion 1020 is wrapped around the outer peripheral surface (outer peripheral surface of the intestinal wall) of the jejunum B2 (refer to FIG. 45). Since the main body portion 1020 is formed in the arc shape, the operator can easily wrap the main body portion 1020 around the outer circumferential surface of the jejunum B2. To form the arc shape for the main body portion 1020, it is possible to employ a method of molding the main body portion 1020 into the arc shape when the medical device 1010 is manufactured.

A first connection portion 1021*a* is placed on an outer surface of a first end portion 1021 positioned in a peripheral edge portion of the main body portion 1020. In addition, a second connection portion 1022*a* is placed on an inner surface of a second end portion 1022 on the opposite side paired with the first end portion 1021. The first end portion 1021 and the second end portion 1022 are configured to be connectable to and separable from each other. Therefore, in a state where the main body portion 1020 is wrapped around an outer peripheral surface of the jejunum B2, the operator brings the second connection portion 1021b positioned on the inner surface of the second end portion 1022 into contact with the first connection portion 1021a positioned on the outer surface of the first end portion 1021. In this manner, the first end portion 1021 and the second end portion 1022 can be connected to each other (refer to FIGS. 45 and 46). The operator can fix the main body portion 1020 to the jejunum B2 by connecting the respective connection portions 1021a and 1022a to each other.

As long as the first connection portion 1021a and the second connection portion 1022a can be connected to each other, a specific configuration thereof is not particularly limited. The respective connection portions 1021a and 1022a may be configured so that both of these can be easily connected to each other by applying a relatively weak force to between the end portions 1021 and 1022. In this example, the respective connection portions 1021a and 1022a may be configured to include a biocompatible magnet or a biocompatible surface fastener.

The respective connection portions 1021a and 1022a may not have a structure integrally attached to the main body portion 1020. For example, the respective connection portions 1021a and 1021b may be biocompatible adhesives applied to the respective end portions 1021a and 1022a when the main body portion 1020 is fixed, or sutures attached to the respective end portions 1021a and 1022a. In a case of using the suture, in a state where the main body portion 1020 is wrapped around the outer peripheral surface of the jejunum B2, the main body portion 1020 can be fixed to the jejunum B2 by further wrapping the suture around the jejunum B2. For example, the suture may be used to fix the main body portion 1020 to the jejunum B2 by suturing the main body portion 1020 to the jejunum B2. In addition, in a case where the suture is attached to the main body portion 1020, the respective end portions 1021 and 1022 of the main body portion 1020 may have a frame portion having no through-holes 25, which is configured to partially improve the strength of the main body portion 1020. The suture may be sutured to the frame portion disposed in the main body portion 1020. In this manner, when an external force is applied to the main body portion 1020 via the suture, it is possible to prevent the main body portion 1020 from being damaged.

A position for placing the respective connection portions 1021a and 1021b in the main body portion 1020 is not particularly limited as long as the main body portion 1020 can be fixed to the jejunum B2 by connecting portions of the main body portion 1020 to each other when the main body portion 1020 is wrapped along the outer peripheral surface of the jejunum B2. Therefore, the connection portions 1021a and 1021b may be placed in portions other than the respective end portions 1021 and 1022 of the main body portion 1020, or the connection portions 1021a and 1022a may be placed in only a portion of the respective end portions 1021 and 1022.

The main body portion 1020 may be formed in a size and a shape so that the outer peripheral surface of the jejunum B2 can be covered in the entire circumferential direction. However, the size and the shape of the main body portion 1020 are not so limited. For example, in a natural state where no external force is applied, the main body portion 1020 may not have the arc shape as illustrated in FIG. 44.

Next, a procedure example of the treatment method according to the second embodiment using the third alternative embodiment of the medical device will be described. The procedure may be the same as that previously described in conjunction with the second embodiment above and will be omitted in the following description.

Figure 45:
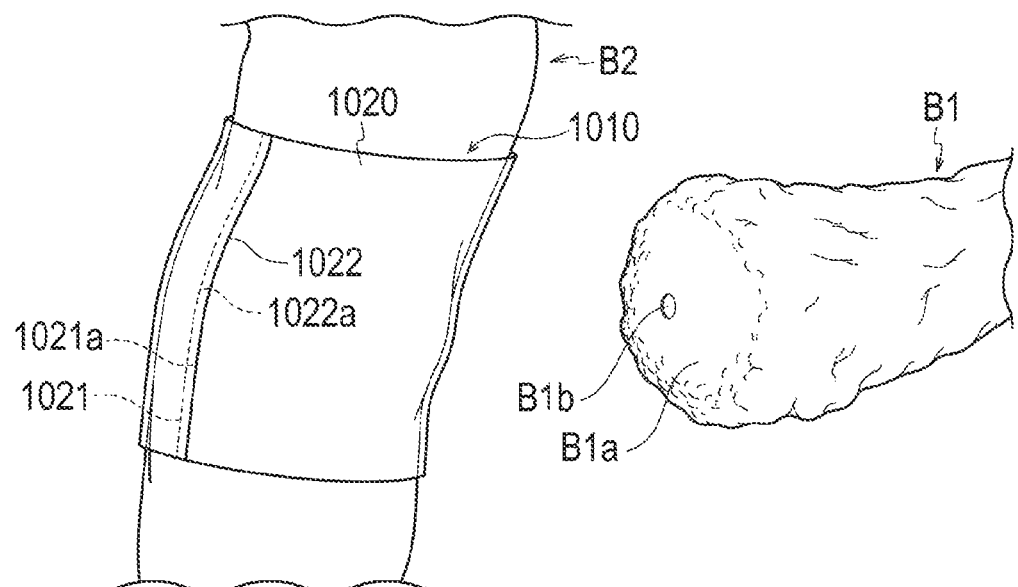
FIG. 45 is a schematic perspective view illustrating a state of the treatment method according to the second embodiment using the third alternative embodiment of the medical device.

As illustrated in FIG. 45, the operator places the main body portion 1020 of the medical device 1010 between the pancreatic parenchyma B1 and the jejunum B2 before the pancreatic parenchyma B1 and the jejunum B2 are sutured. In this case, the operator wraps the main body portion 1020 around the outer peripheral surface of the jejunum B2. In addition, the operator may connect the second connection portion 1022a placed on the inner surface of the second end portion 1022 of the main body portion 1020 to the first connection portion 1021a placed on the outer surface of the first end portion 1021 of the main body portion 1020, thereby connecting the connection portions 1022a and 1022b to each other. The respective connection portions 1022a and 1022b may be connected to each other, thereby fixing the main body portion 1020 to the jejunum B2 in a state where the main body portion 1020 is wrapped around the outer peripheral surface of the jejunum B2. The main body portion 1020 may be fixed to the jejunum B2 by the operator, thereby enabling the operator to prevent the main body portion 1020 from being detached from, or misaligned with, the jejunum B2 or to prevent the main body portion 1020 from being deformed during each treatment subsequent thereto.

Figure 46:
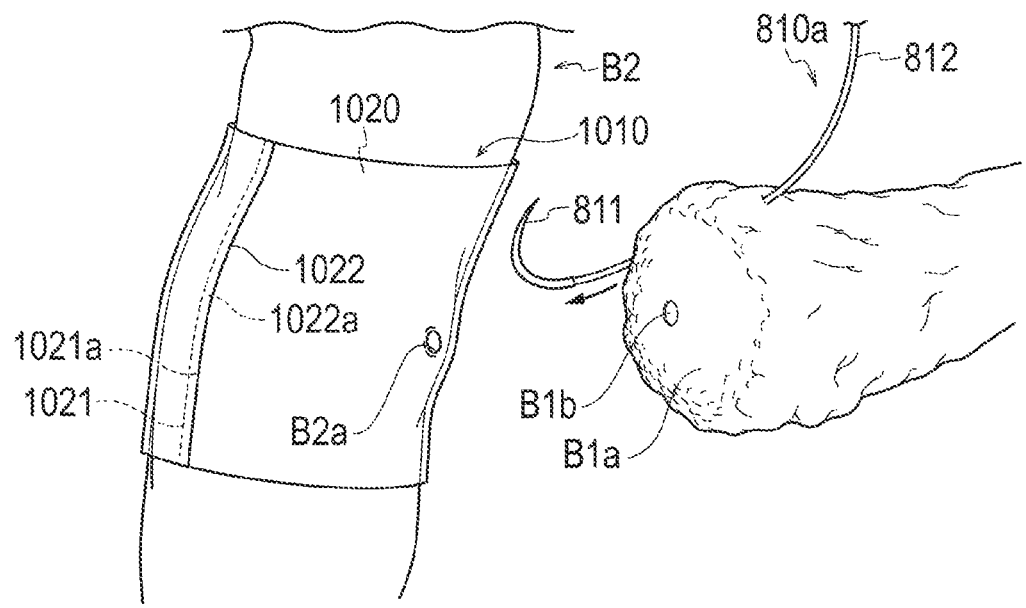
FIG. 46 is a schematic perspective view illustrating a state of the treatment method according to the second embodiment using the third alternative embodiment of the medical device.

Next, as illustrated in FIG. 46, the operator forms a through-hole B2a penetrating the interior and the exterior of the jejunum B2 on a jejunum serosal surface of the jejunum B2. A through-hole (not illustrated) is also formed at a position corresponding to the through-hole B2a in the main body portion 1020 fixed to the jejunum B2. The through-hole may be formed in the main body portion 1020 before the main body portion 1020 is fixed the jejunum B2.

Figure 47:
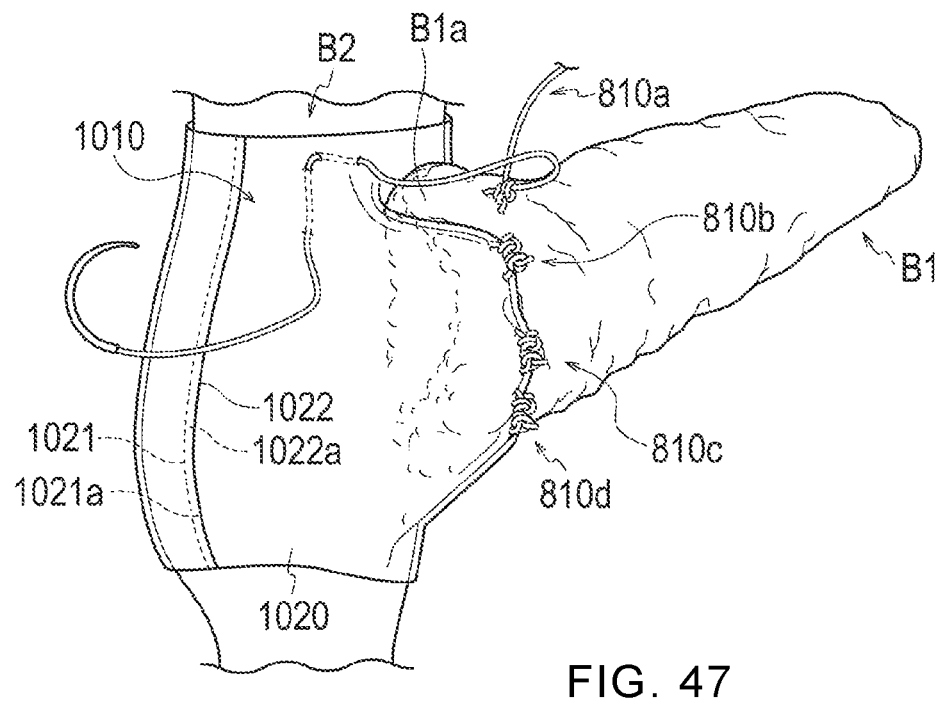
FIG. 47 is a schematic perspective view illustrating a state of the treatment method according to the second embodiment using the third alternative embodiment of the medical device.

Next, the operator performs the suturing by operating the double end needle 810a from the pancreatic parenchyma B1 side to the jejunum B2 side. In addition, as illustrated in FIG. 47, the operator uses the double end needles 810a, 810b, 811c, and 810d. In a state where a portion of the main body portion 1020 is interposed between the cut surface B1a of the pancreatic parenchyma B1 and the intestinal wall of the jejunum B2, the operator sutures (fixes) the jejunum. B2, the pancreatic parenchyma B1, and the main body portion 1020. Although not illustrated, the operator carries out work for allowing the interior of the jejunum B2 and the pancreatic duct B1b to communicate with each other via the through-hole B2a and the pancreatic duct tube 830 (refer to FIG. 20) before the jejunum B2, the pancreatic parenchyma B1, and the main body portion 1020 are sutured.

Figure 48:
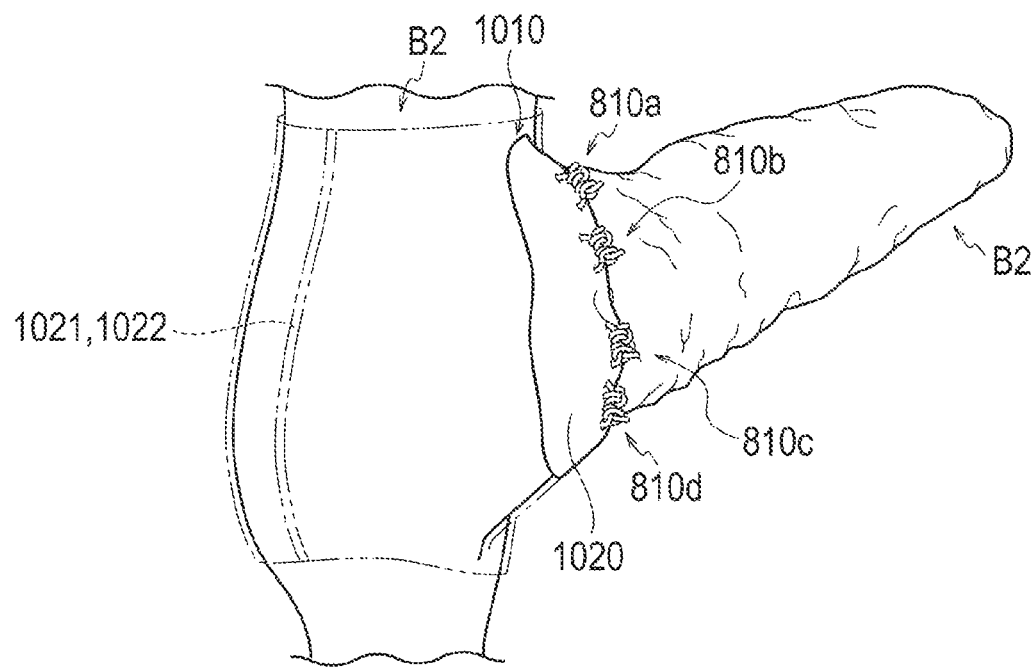
FIG. 48 is a schematic perspective view illustrating a state of the treatment method according to the second embodiment using the third alternative embodiment of the medical device.

After the jejunum B2, the pancreatic parenchyma B1, and the main body portion 1020 are sutured, the operator can cut and remove a portion which is not placed between the cut surface B1a of the pancreatic parenchyma B1 and the jejunum B2 in the main body portion 1020 (portion which does not promote the adhesion between the pancreatic parenchyma B1 and the intestinal wall). For example, the portions to be cut and separated are the respective end portions 1021 and 1022 of the main body portion 1020 or any desired portion including the respective end portions 1021 and 1022. A cut line for cutting and removing the respective end portions 1021 and 1022 may be formed in advance in the main body portion 1020. In FIG. 48, the main body portion 1020 before cutting is schematically illustrated using a two-dot chain line.

The operator causes the medical device 1010 to indwell in a state where a portion of the main body portion 1020 of the medical device 1010 is interposed between the cut surface B1*a* of the pancreatic parenchyma B1 and the intestinal wall of the jejunum B2. While the main body portion 1020 of the medical device 1010 comes into contact with the cut surface B1*a* of the pancreatic parenchyma B1 and the intestinal wall of the jejunum B2, the main body portion 1020 of the medical device 1010 is caused to indwell between the cut surface B1*a* of the pancreatic parenchyma B1 and the intestinal wall of the jejunum B2, thereby promoting the adhesion between the biological tissue of the pancreatic parenchyma B1 and the biological tissue of the intestinal wall of the jejunum B2.

As described above, according to the treatment method of the present modification example, before the main body portion 1020 of the medical device 1010 is interposed between the pancreatic parenchyma B1 and the jejunum B2, the main body portion 1020 is fixed to the jejunum B2 in a state where the main body portion 1020 is wrapped around the jejunum B2. Therefore, while the pancreatic parenchyma-jejunum anastomosis is performed, it is possible to prevent the main body portion 1020 wrapped around the outer peripheral surface of the jejunum B2 from being detached from or misaligned with the jejunum B2 or to prevent the main body portion 1020 from being deformed. In this manner, the pancreatic parenchyma-jejunum anastomosis can be smoothly and easily performed.

A usage of the medical device 1010 described in conjunction with the examples provided above are not limited to the pancreatic parenchyma-jejunum anastomosis, and may also be applicable to other medical procedures.

The treatment methods according to the present disclosure have been described with reference to various embodiments and examples. However, the present disclosure is not limited only to the contents described in conjunction with these embodiments or examples, and can be modified with reference to the appended claims.

For example, the biological organ to be joined, the joint target site, and the specific medical procedure are not limited to those described in the embodiments. In addition, the material, the size, the shape, and the specific structure of the medical device are not limited as long as the main body portion included in the medical device promotes the adhesion between the biological tissues of the joint target sites.

Embodiments include a treatment method comprising: placing a medical device including a sheet-like main body portion for promoting adhesion between biological tissues between one joint target site and another joint target site of a biological organ to be joined; and joining the one joint target site and the other joint target site to each other in a state where at least a portion of the main body portion of the medical device is interposed between the one joint target site and the other joint target site.

Aspects of the above treatment method further comprise: bringing at least a portion of the main body portion of the medical device into contact with the one joint target site and/or the other joint target site, when the medical device is placed. Aspects of any of the above treatment methods further comprise: interposing the main body portion of the medical device between the one joint target site and the other joint target site by moving the one joint target site and the other joint target site relatively closer to each other, in a state where the main body portion of the medical device is placed between the one joint target site and the other joint target site. Aspects of any of the above treatment methods include wherein in the joining, while the one joint target site and the other joint target site are joined to each other, at least a portion of the main body portion is joined to the one joint target site and/or the other joint target site. Aspects of any of the above treatment methods include wherein the joining is performed using a stapler and/or a suture. Aspects of any of the above treatment methods include wherein the biological organ to be joined is a large intestine, wherein the one joint target site is a mouth portion periphery of the large intestine, and wherein the other joint target site is an intestinal wall of the large intestine. Aspects of the above treatment methods further comprise: placing a first engagement instrument of an anastomosis device in a mouth portion of the large intestine; and placing a second engagement instrument of the anastomosis device in a through-hole formed on the intestinal wall of the large intestine, wherein the main body portion comprises a hole portion which enables the medical device to be mounted on the first engagement instrument or the second engagement instrument, and wherein in a state where the medical device is mounted on the first engagement instrument or the second engagement instrument, the main body portion is interposed between the mouth portion periphery of the large intestine and the intestinal wall of the large intestine by moving the mouth portion periphery of the large intestine and the intestinal wall of the large intestine relatively closer to each other. Aspects of the above treatment methods include wherein the biological organs to be joined are a pancreatic parenchyma and a jejunum, wherein the one joint target site is a cut surface periphery of the cut pancreatic parenchyma, and wherein the other joint target site is an intestinal wall of the jejunum. Aspects of at least one of the above treatment methods include wherein the main body portion comprises a hole portion which is aligned with a pancreatic duct extending inside the pancreatic parenchyma and a through-hole formed on the intestine wall of the jejunum, and wherein in a state where the main body portion is brought into contact with the cut surface periphery of the pancreatic parenchyma or a periphery of the through-hole formed on the intestinal wall of the jejunum, the main body portion is interposed between the pancreatic parenchyma and the jejunum by moving the pancreatic parenchyma and the jejunum relatively closer to each other. Aspects of at least one of the above treatment methods include wherein the medical device comprises a first tubular portion having a lumen and a second tubular portion having a lumen, wherein the first tubular portion is inserted into the pancreatic duct, and wherein the second tubular portion is inserted into the through-hole formed on the intestinal wall of the jejunum. Aspects of at least one of the above treatment methods further comprise: fixing the main body portion to the jejunum in a state where the main body portion is wrapped around the jejunum, before the main body portion is interposed between the pancreatic parenchyma and the jejunum. Aspects of at least one of the above treatment methods include wherein the biological organs to be joined are an esophagus and a biological organ other than the esophagus, wherein the one joint target site is a mouth portion periphery of the esophagus, and wherein the other joint target site is a mouth portion periphery of the biological organ other than the esophagus, which is joined to a mouth portion of the esophagus. Aspects of the above treatment methods include wherein in a state where the main body portion is placed between the mouth portion periphery of the esophagus and the mouth portion periphery of the biological organ other than the esophagus, the main body portion is interposed between the mouth portion periphery of the esophagus and the mouth portion periphery of the biological organ other than the esophagus by moving the mouth portion of the esophagus and the mouth portion of the biological organ other than the esophagus relatively closer to each other. Aspects of the above treatment methods include wherein the mouth portion periphery of the esophagus and the mouth portion periphery of the biological organ other than the esophagus are joined to each other at a plurality of different locations in a circumferential direction of the esophagus, in a state where the main body portion is interposed between the mouth portion periphery of the esophagus and the mouth portion periphery of the biological organ other than the esophagus. Aspects of at least one of the above treatment methods include wherein the medical device comprises a guide portion which guides a joint position for joining the main body portion to the mouth portion periphery of the esophagus and the mouth portion periphery of the biological organ other than the esophagus, and wherein when the mouth portion periphery of the esophagus and the mouth portion periphery of the biological organ other than the esophagus are joined to each other, the joint position of the main body portion is controlled using the guide portion. Aspects of any of the above treatment methods include wherein the main body portion comprises a through-hole penetrating the main body portion in a thickness direction. Aspects of any of the above treatment methods include wherein joining the one joint target site and the other joint target site comprises forming a continuous seal between the one joint target site and the other joint target site around a periphery of a portion of the main body portion.

Embodiments include a treatment method comprising: placing a medical device including a sheet-like main body portion for promoting adhesion between biological tissues between a mouth portion periphery of a large intestine and an intestinal wall of the large intestine; and joining the mouth portion periphery of the large intestine and the intestinal wall of the large intestine to each other in a state where at least a portion of the main body portion of the medical device is interposed between the mouth portion periphery of the large intestine and the intestinal wall of the large intestine.

Embodiments include a treatment method comprising: placing a medical device including a sheet-like main body portion for promoting adhesion between biological tissues between a cut surface periphery of a pancreatic parenchyma and an intestinal wall of a jejunum; and joining a cut surface of the pancreatic parenchyma and the intestinal wall of the jejunum to each other in a state where at least a portion of the main body portion of the medical device is interposed between the cut surface periphery of the pancreatic parenchyma and the intestinal wall of the jejunum.

Embodiments include a treatment method comprising: placing a medical device including a sheet-like main body portion for promoting adhesion between biological tissues between a mouth portion periphery of an esophagus and a mouth portion periphery of a biological organ other than the esophagus; and joining the mouth portion periphery of the esophagus and the mouth portion periphery of the biological organ other than the esophagus to each other in a state where at least a portion of the main body portion of the medical device is interposed between the mouth portion periphery of the esophagus and the mouth portion periphery of the biological organ other than the esophagus.

Any one or more of the aspects/embodiments as substantially disclosed herein.

Any one or more of the aspects/embodiments as substantially disclosed herein optionally in combination with any one or more other aspects/embodiments as substantially disclosed herein.

One or more means adapted to perform any one or more of the above aspects/embodiments as substantially disclosed herein.

DESCRIPTION OF REFERENCE CHARACTERS 10, 110, 210, 310, 410, 510, 610, 1010 medical device,
20, 120, 220, 320, 420, 520, 620, 1020 main body portion,
25 through-hole,
130, 230, 330, 430 hole portion,
240 slit,
321 first split piece,
322 second split piece,
450 first tubular portion,
460 second tubular portion,
570 guide portion,
680 protruding portion,
A1 mouth side of the large intestine,
A2 anal side of the large intestine,
B1 pancreatic parenchyma,
B2 jejunum,
C1 esophagus,
C2 gastric tube (biological organ other than esophagus)

What is claimed is:

1. A treatment method comprising:
providing a sheet-like main body portion of a medical device for promoting adhesion between biological tissues between a first joint target site and a second joint target site of a biological organ to be joined, the main body portion comprising a first split piece and a second split piece separated from the first split piece by at least one slit running from a periphery of the main body portion to a hole portion disposed in the main body portion;
placing the first split piece into contact with a first area of one of the first joint target site and the second joint target site;
joining the first joint target site and the second joint target site to each other in a state where at least a portion of the first split piece of the main body portion of the medical device is interposed between the first joint target site and the second joint target site at the first area;
placing the second split piece into contact with a second area of one of the first joint target site and the second joint target site such that the second split piece is arranged adjacent to the first split piece; and
joining the first joint target site and the second joint target site to each other in a state where at least a portion of the second split piece of the main body portion of the medical device is interposed between the first joint target site and the second joint target site at the second area.

2. The treatment method according to claim 1, further comprising:
bringing at least a portion of the main body portion of the medical device into contact with at least one of the first joint target site and the second joint target site, when at least one of the first split piece and the second split piece of the medical device is placed.

3. The treatment method according to claim 1, further comprising:
fixing the main body portion of the medical device between the first joint target site and the second joint target site by moving the first joint target site and the second joint target site relatively closer to each other, in a state where the main body portion of the medical device is placed into contact with both the first joint target site and the second joint target site.

4. The treatment method according to claim 1,
wherein in the joining, while the first joint target site and the second joint target site are joined to each other, at least a portion of the main body portion is joined to at least one of the first joint target site and the second joint target site.

5. The treatment method according to claim 1,
wherein the joining is performed using at least one of a stapler and a suture.

6. The treatment method according to claim 1,
wherein the biological organ to be joined is a large intestine,
wherein the first joint target site is a mouth portion periphery of the large intestine, and
wherein the second joint target site is an intestinal wall of the large intestine.

7. The treatment method according to claim 6, further comprising:
placing a first engagement instrument of an anastomosis device in a mouth portion of the large intestine; and
placing a second engagement instrument of the anastomosis device in a through-hole formed on the intestinal wall of the large intestine,
wherein the hole portion enables the medical device to be mounted on the first engagement instrument or the second engagement instrument, and
wherein in a state where the medical device is mounted on the first engagement instrument or the second engagement instrument, the main body portion is interposed between the mouth portion periphery of the large intestine and the intestinal wall of the large intestine by moving the mouth portion periphery of the large intestine and the intestinal wall of the large intestine relatively closer to each other.

8. The treatment method according to claim 1,
wherein the biological organ to be joined comprises a pancreatic parenchyma and a jejunum,
wherein the first joint target site is a cut surface periphery of the cut pancreatic parenchyma, and
wherein the second joint target site is an intestinal wall of the jejunum.

9. The treatment method according to claim 8,
wherein the hole portion disposed in the main body portion is aligned with a pancreatic duct extending inside the pancreatic parenchyma and a hole formed at the second joint target site, and
wherein in a state where the main body portion is brought into contact with the cut surface periphery of the pancreatic parenchyma or a periphery of the hole formed at the second joint target site, the main body portion is interposed between the pancreatic parenchyma and the jejunum by moving the pancreatic parenchyma and the jejunum relatively closer to each other.

10. The treatment method according to claim 8,
wherein the medical device comprises a first tubular portion formed of a same material as the main body portion, and wherein the first tubular portion comprises a first plurality of through-holes disposed around a periphery thereof,
wherein a second tubular portion of the medical device is formed of the same material as the main body portion and the first tubular portion, and wherein the second tubular portion comprises a second plurality of through-holes disposed around a periphery thereof; and
wherein the main body portion comprises a third plurality of through-holes running through the main body portion from the first surface side to the second surface side.

11. The treatment method according to claim 8, further comprising:
fixing the main body portion to the jejunum in a state where the main body portion is wrapped around the jejunum before the main body portion is interposed between the pancreatic parenchyma and the jejunum.

12. The treatment method according to claim 1,
wherein the biological organ to be joined comprises an esophagus and a biological organ other than the esophagus,
wherein the first joint target site is a mouth portion periphery of the esophagus, and
wherein the second joint target site is a mouth portion periphery of the biological organ other than the esophagus, which is joined to the mouth portion of the esophagus.

13. The treatment method according to claim 12,
wherein in a state where the main body portion is placed between the mouth portion periphery of the esophagus and the mouth portion periphery of the biological organ other than the esophagus, the main body portion is interposed between the mouth portion periphery of the esophagus and the mouth portion periphery of the biological organ other than the esophagus by moving the mouth portion of the esophagus and the mouth portion of the biological organ other than the esophagus relatively closer to each other.

14. The treatment method according to claim 13,
wherein the mouth portion periphery of the esophagus and the mouth portion periphery of the biological organ other than the esophagus are joined to each other at a plurality of different locations in a circumferential direction of the esophagus, in a state where the main body portion is interposed between the mouth portion periphery of the esophagus and the mouth portion periphery of the biological organ other than the esophagus.

15. The treatment method according to claim 1,
wherein the main body portion comprises a plurality of through-holes running through the main body portion from a first surface side to a second surface side thereof.

16. The treatment method according to claim 1,
wherein joining the first joint target site and the second joint target site comprises forming a continuous seal between the first joint target site and the second joint target site around a periphery of a portion of the main body portion.

17. A treatment method for large intestine anastomosis comprising:
providing a sheet-like main body portion of a medical device for promoting adhesion between biological tissues between a mouth portion periphery of a large intestine and an intestinal wall of the large intestine, the main body portion comprising a first split piece and a second split piece separated from the first split piece by at least one slit running from a periphery of the main body portion to a hole portion disposed in the main body portion;
placing the first split piece into contact with a first area of the mouth portion periphery of the large intestine;
joining the mouth portion periphery of the large intestine and the intestinal wall of the large intestine to each other in a state where at least a portion of the first split piece of the main body portion of the medical device is interposed between the mouth portion periphery of the large intestine and the intestinal wall of the large intestine at the first area;

placing the second split piece into contact with a second area of the mouth portion periphery of the large intestine such that the second split piece is arranged adjacent to the first split piece; and joining the mouth portion periphery of the large intestine and the intestinal wall of the large intestine to each other in a state where at least a portion of the second split piece of the main body portion of the medical device is interposed between the mouth portion periphery of the large intestine and the intestinal wall of the large intestine at the second area.

18. A treatment method comprising:

placing a sheet-like main body portion of a medical device for promoting adhesion between biological tissues between a cut cross section periphery of a pancreatic parenchyma and an intestinal wall of a jejunum, comprising:

inserting a hollow first tubular portion of the medical device into a pancreatic duct formed in the cut cross section periphery of a pancreatic parenchyma, the first tubular portion formed on a first surface side of the main body portion and protruding in a direction away from the first surface side, the first tubular portion comprising a first lumen; and inserting a hollow second tubular portion of the medical device into a hole formed in the intestinal wall of the jejunum, the second tubular portion formed on an opposite second surface side of the main body portion and protruding in a direction away from the second surface side, the second tubular portion comprising a second lumen; and joining a cut surface of the pancreatic parenchyma and the intestinal wall of the jejunum to each other in a state where at least a portion of the main body portion of the medical device is interposed between the cut cross section periphery of the pancreatic parenchyma and the intestinal wall of the jejunum and, when joined, a fluid communication path is established running from the first lumen of the first tubular portion through a hole portion disposed in the main body portion and through the second lumen of the second tubular portion.

19. A treatment method comprising:

placing a sheet-like main body portion of a medical device for promoting adhesion between biological tissues between a mouth portion periphery of an esophagus and a mouth portion periphery of a biological organ other than the esophagus, wherein the medical device comprises a guide portion extending in a substantially perpendicular direction to a planar surface of the main body portion, wherein the body portion comprises a first plurality of through-holes disposed therein, and wherein the guide portion comprises a second plurality of through-holes disposed in at least one surface of the guide portion; and joining the mouth portion periphery of the esophagus and the mouth portion periphery of the biological organ other than the esophagus to each other in a state where at least a portion of the main body portion of the medical device is interposed between the mouth portion periphery of the esophagus and the mouth portion periphery of the biological organ other than the esophagus and the guide portion is disposed outside of the mouth portion periphery of the esophagus and the mouth portion periphery of the biological organ other than the esophagus.

\* \* \* \* \*